US010646538B2

(12) United States Patent
Ulijn et al.

(10) Patent No.: US 10,646,538 B2
(45) Date of Patent: May 12, 2020

(54) SELF-ASSEMBLING TRIPEPTIDES

(71) Applicant: ENDO Biologics, Inc., Venice, CA (US)

(72) Inventors: Rein Ulijn, Glasgow (GB); Tell Tuttle, Glasgow (GB); Pim Frederix, Glasgow (GB); Gary Scott, Glasgow (GB); Yousef Abul-Haija, Glasgow (GB)

(73) Assignee: ENDO Biologics, Inc., Venice, CA (US)

( * ) Notice: Subject to any disclaimer, the term of this patent is extended or adjusted under 35 U.S.C. 154(b) by 62 days.

(21) Appl. No.: 15/517,839

(22) PCT Filed: Oct. 9, 2015

(86) PCT No.: PCT/GB2015/052972
§ 371 (c)(1),
(2) Date: Apr. 7, 2017

(87) PCT Pub. No.: WO2016/055810
PCT Pub. Date: Apr. 14, 2016

(65) Prior Publication Data
US 2017/0246237 A1 Aug. 31, 2017

(30) Foreign Application Priority Data

Oct. 9, 2014 (GB) .................................. 1417885.9
Dec. 22, 2014 (GB) .................................. 1422993.4

(51) Int. Cl.
*A61K 38/06* (2006.01)
*C07K 5/087* (2006.01)
(Continued)

(52) U.S. Cl.
CPC ............ *A61K 38/06* (2013.01); *A61K 9/0014* (2013.01); *A61L 15/60* (2013.01); *B82Y 40/00* (2013.01);
(Continued)

(58) Field of Classification Search
CPC ....... A61K 38/06; A61K 9/0014; A61L 15/60; B82Y 40/00; C07K 5/0812; C07K 5/0815; G16B 15/00
See application file for complete search history.

(56) References Cited

U.S. PATENT DOCUMENTS

| 2004/0214184 A1* | 10/2004 | Skubitz | ................... | C07K 5/06 435/6.12 |
| 2009/0263429 A1* | 10/2009 | Ulijn | ................... | A61L 26/008 424/400 |
| 2013/0252880 A1* | 9/2013 | Kallenbach | ............ | A61K 38/10 514/2.4 |

FOREIGN PATENT DOCUMENTS

| WO | WO 01/27261 | 4/2001 |
| WO | WO 2011/131671 | 10/2011 |

(Continued)

OTHER PUBLICATIONS

Guo et al., Triphenylalanine peptides self-assemble into nanospheres and nanorods that are different from the nanovesicles and nanotubes formed by diphenylalanine peptides, Nanoscale, vol. 6:2800-2811 (2014) (Year: 2014).*

(Continued)

*Primary Examiner* — Randall L Beane
(74) *Attorney, Agent, or Firm* — Casimir Jones, S.C.; Robert A. Goetz

(57) ABSTRACT

The present invention relates to a method of predicting the propensity of tripeptides to from aggregates in solution. The present invention also provides tripeptides which are able to form aggregates in solution, as well as uses thereof. The present invention also provides nanostructures formed by self-aggregation of tripeptides of the present invention. The present invention also provides pH responsive aggregates as (Continued)

well as methods of screening for the ability of a tripeptide to form a pH dependent aggregate or gel.

**9 Claims, 8 Drawing Sheets
(6 of 8 Drawing Sheet(s) Filed in Color)**

(51) Int. Cl.
*C07K 5/09* (2006.01)
*G16B 15/00* (2019.01)
*B82Y 40/00* (2011.01)
*A61K 9/00* (2006.01)
*A61L 15/60* (2006.01)

(52) U.S. Cl.
CPC .......... *C07K 5/0812* (2013.01); *C07K 5/0815* (2013.01); *G16B 15/00* (2019.02)

(56) References Cited

FOREIGN PATENT DOCUMENTS

WO　　WO-2014120886 A1 *　8/2014　........... A01N 1/0231
WO　　WO 2015/177569　　11/2015

OTHER PUBLICATIONS

Smadbeck et al., De Novo Design and Experimental Characterization of Ultrashort Self-Associating Peptides, PLoS Comput. Biol., vol. 10(7):e1003718, 24 pages, including supplemental S1 and S2 (published online Jul. 10, 2014) (Year: 2014).*
Ash, W. L., Zlomislic, M. R., Oloo, E. O. & Tieleman, D. P. Computer simulations of membrane proteins. Biochim. Biophys. Acta BBA—Biomembr. 1666, 158-189 (2004).
Barth, A. & Zscherp, C. What Vibrations Tell About Proteins. Q. Rev. Biophys. 35, 369-430 (2002).
Berendsen, H. J. C.; Postma, J. P. M.; van Gunsteren, W. F.; DiNola, A.; Haak, J. R. J. Chem. Phys. 1984, 81, 3684.
Chen, L., Revel, S., Morris, K., C. Serpell, L. & Adams, D. J. Effect of Molecular Structure on the Properties of Naphthalene-Dipeptide Hydrogelators. Langmuir 26, 13466-13471 (2010).
Cohen, Y., Avram, L. & Frish, L. Diffusion NMR Spectroscopy in Supramolecular and Combinatorial Chemistry: An Old Parameter—New Insights. Angew. Chem. Int. Ed. 44, 520-554 (2005).
Das, A. K., Bose, P. P., Drew, M. G. B. & Banerjee, A. The role of protecting groups in the formation of organogels through a nanofibrillar network formed by self-assembling terminally protected tripeptides. Tetrahedron 63, 7432-7442 (2007).
Degrado, W. F. & Lear, J. D. Induction of peptide conformation at apolar water interfaces. 1. A study with model peptides of defined hydrophobic periodicity. J. Am. Chem. Soc. 107, 7684-7689 (1985).
Degrado, W. F. Design of Peptides and Proteins. Adv. Protein Chem. 39, 51-124 (1988).
Frederix et al. "Exploring the sequence space for (tri-)peptide self-assembly to design and discover new hydrogels" Nature Chemistry, vol. 7, No. 1, Dec. 8, 2014, pp. 30-37.
Frederix, P. W. J. M., Ulijn, R. V., Hunt, N. T. & Tuttle, T. Virtual Screening for Dipeptide Aggregation: Toward Predictive Tools for Peptide Self-Assembly. J. Phys. Chem. Lett. 2, 2380-2384 (2011).
Fuhrmans, M. & Marrink, S.-J. A tool for the morphological analysis of mixtures of lipids and water in computer simulations. J. Mol. Model. 17, 1755-1766 (2011).
Ghadiri, M. R., Granja, J. R., Milligan, R. A., McRee, D. E. & Khazanovich, N. Self-assembling organic nanotubes based on a cyclic peptide architecture. Nature 366, 324-327 (1993).
Guo, C., Luo, Y., Zhou, R. & Wei, G. Probing the Self-Assembly Mechanism of Diphenylalanine-Based Peptide Nanovesicles and Nanotubes. ACS Nano 6, 3907-3918 (2012).

Han, T. H. et al. Bionanosphere Lithography via Hierarchical Peptide Self-Assembly of Aromatic Triphenylalanine. Small 6, 945-951 (2010).
Hartgerink, J. D., Benlash E. & Stupp, S. L. Self-Assembly and Mineralization of Peptide-Amphiphile Nanofibers. Science 294, 1684-1688 (2001).
Hauser, C. A. E. et al. Natural tri- to hexapeptides self-assemble in water to amyloid beta-type fiber aggregates by unexpected alpha-helical intermediate structures. Proc. Natl. Acad. Sci. U. S. A. 108, 1361-1366 (2011).
Heldt et al. "Identification of Trimeric Peptides that Bind Porcine Parvovirus from Mixtures Containing Human Blood Plasma" Biotechnology Progress, vol. 24, No. 3, Jun. 6, 2008, pp. 554-560.
Hess, B. J. Chem. Theory Comput. 2008, 4, 116.
Hess, B.; Kutzner, C.; van der Spoel, D.; Lindahl, E. J. Chem. Theory Comput. 2008, 4, 435.
Humphrey, W., Dalke, A. & Schulten, K. VMD: Visual molecular dynamics. J. Mol. Graph. 14, 33-38 (1996).
James, J. & Mandal, A. B. The aggregation of Tyr-Phe dipeptide and Val-Tyr-Val tripeptide in aqueous solution and in the presence of SDS and PEO-PPO-PEO triblock copolymer: Fluorescence spectroscopic studies. J. Colloid Interface Sci. 360, 600-605 (2011).
Lee, O.-S., Cho, V. & Schatz, G. C. Modeling the Self-Assembly of Peptide Amphiphiles into Fibers Using Coarse-Grained Molecular Dynamics. Nano Lett. 12, 4907-4913 (2012).
Lyon, R. P. & Atkins, W. M. Self-Assembly and Gelation of Oxidized Glutathione in Organic Solvents. J. Am. Chem. Soc. 123, 4408-4413 (2001).
Marchesan, S. et al. Unzipping the role of chirality in nanoscale self-assembly of tripeptide hydrogels. Nanoscale 4, 6752-6760 (2012).
Marchesan, S., Easton, C. D., Kushkaki, F., Waddington, L. & Hartley, P. G. Tripeptide self-assembled hydrogels: unexpected twists of chirality. Chem. Commun. 48, 2195-2197 (2012).
Marrink, S. J.; de Vries, A. H.; Mark, A. E. J. Phys. Chem. B 2004, 108, 750.
Marrink, S. J.; Risselada, H. J.; Yefimov, S.; Tieleman, D. P.; de Vries, A. H. J. Phys. Chem. B 2007, 111, 7812.
McCullagh, M., Prytkova, T., Tonzani, S., Winter, N. D. & Schatz, G. C. Modeling Self-Assembly Processes Driven by Nonbonded Interactions in Soft Materials†. J. Phys. Chem. B 112, 10388-10398 (2008).
Monticelli, L. et al. The MARTINI Coarse-Grained Force Field: Extension to Proteins. J. Chem. Theory Comput. 4, 819-834 (2008).
Motamedi et al. "Theoretical investigation on the binding of lysine-containing peptides with dodecyl sulfate ion using semi-empirical calculations" Journal of Molecular Structure, vol. 806, No. 1-3, Feb. 11, 2007, pp. 205-211.
O'Leary, L. E. R., Fallas, J. A., Bakota, E. L., Kang, M. K. & Hartgerink, J. D. Multi-hierarchical self-assembly of a collagen mimetic peptide from triple helix to nanofibre and hydrogel. Nat. Chem. 3, 821-828 (2011).
Pouget, E. et al. Elucidation of the Self-Assembly Pathway of Lanreotide Octapeptide into beta-Sheet Nanotubes: Role of Two Stable Intermediates. J. Am. Chem. Soc. 132, 4230-4241 (2010).
Reches, M. & Gazit, E. Casting metal nanowires within discrete self-assembled peptide nanotubes. Science 300, 625-627 (2003).
Reches, M. & Gazit, E. Formation of Closed-Cage Nanostructures by Self-Assembly of Aromatic Dipeptides. Nano Lett. 4, 581-585 (2004).
Reches, M., Porat, Y. & Gazit, E. Amyloid Fibril Formation by Pentapeptide and Tetrapeptide Fragments of Human Calcitonin. J. Biol. Chem. 277, 35475-35480 (2002).
Singh, G. & Tieleman, D. P. Using the Wimley-White Hydrophobicity Scale as a Direct Quantitative Test of Force Fields: The MARTINI Coarse-Grained Model. J. Chem. Theory Comput. 7, 2316-2324 (2011).
Smith, A. M. & Ulijn, R. V. Designing peptide based nanomaterials—Chemical Society Reviews (RSC Publishing). Chem. Soc. Rev. 37, 664-675 (2008).

(56) References Cited

OTHER PUBLICATIONS

Subbalakshmi, C., Manorama, S. V. & Nagaraj, R. Self-assembly of short peptides composed of only aliphatic amino acids and a combination of aromatic and aliphatic amino acids. J. Pept. Sci. 18, 283-292 (2012).

Tamamis, P. et al. Self-Assembly of Phenylalanine Oligopeptides: Insights from Experiments and Simulations. Biophys. J. 96, 5020-5029 (2009).

Thirumalai, D., Klimov, D. & Dima, R. Emerging ideas on the molecular basis of protein and peptide aggregation. Curr. Opin. Struct. Biol. 13, 146-159 (2003).

White, S. H. & Wimley, W. C. Hydrophobic interactions of peptides with membrane interfaces. Biochim. Biophys. Acta BBA—Rev. Biomembr. 1376, 339-352 (1998).

Wimley, W. C., Creamer, T. P. & White, S. H. Solvation Energies of Amino Acid Side Chains and Backbone in a Family of Host-Guest Pentapeptides†. Biochemistry (Mosc.) 35, 5109-5124 (1996).

Wu, C., Lei, H. & Duan, Y. Formation of Partially Ordered Oligomers of Amyloidogenic Hexapeptide (NFGAIL) in Aqueous Solution Observed in Molecular Dynamics Simulations. Biophys. J. 87, 3000-3009 (2004).

Yang, Z., Liang, G., Ma, M., Gao, Y. & Xu, B. Conjugates of naphthalene and dipeptides produce molecular hydrogelators with high efficiency of hydrogelation and superhelical nanofibers. J. Mater. Chem. 17, 850-854 (2007).

Yesylevskyy, S. O., Schäfer, L. V., Sengupta, D. & Marrink, S. J. Polarizable Water Model for the Coarse-Grained MARTINI Force Field. PLoS Comput Biol 6, e1000810 (2010).

Zaccai, N. R. et al. A de novo peptide hexamer with a mutable channel. Nat. Chem. Biol. 7, 935-941 (2011).

Zhang, S. G. Fabrication of novel biomaterials through molecular self-assembly. Nat. Biotechnol. 21, 1171-1178 (2003).

Zhang, S., Holmes, T., Lockshin, C. & Rich, A. Spontaneous assembly of a self-complementary oligopeptide to form a stable macroscopic membrane. Proc. Natl. Acad. Sci. U. S. A. 90, 3334-3338 (1993).

Zhang, Y., Gu, H., Yang, Z. & Xu, B. Supramolecular Hydrogels Respond to Ligand-Receptor Interaction. J. Am. Chem. Soc. 125, 13680-13681 (2003).

Search Report, Intellectual Property Office, dated Jun. 24, 2015, South Wales NP10 8QQ, United Kingdom.

Cao, M., Cao, C., Zhang, L., Xia, D. & Xu, H. Tuning of peptide assembly through force balance adjustment. J. Colloid Interface Sci. 407, 287-295 published—Feb. 7, 2013.

De Jong, D. H. et al. Improved Parameters for the Martini Coarse-Grained Protein Force Field. J. Chem. Theory Comput. 9, 687-697 published Nov. 14, 2012.

Fleming, S. et al. Assessing the Utility of Infrared Spectroscopy as a Structural Diagnostic Tool for β-Sheets in Self-Assembling Aromatic Peptide Amphiphiles. Langmuir 29, 9510-9515 published Jun. 27, 2013.

Fletcher, J. M. et al. Self-Assembling Cages from Coiled-Coil Peptide Modules. Science 340, 595-599 (May 2013).

Georgoulia, P. S. & Glykos, N. M. On the Foldability of Tryptophan-Containing Tetra- and Pentapeptides: An Exhaustive Molecular Dynamics Study. J. Phys. Chem. B 117, 5522-5532 published Mar. 5, 2013.

Guo, C., Luo, Y., Zhou, R. & Wei, G. Triphenylalanine peptides self-assemble into nanospheres and nanorods that are different from the nanovesicles and nanotubes formed by diphenylalanine peptides. Nanoscale published Feb. 1, 2014. doi:10.1039/c3nr02505e.

Marchesan, S. et al. Chirality effects at each amino acid position on tripeptide self-assembly into hydrogel biomaterials. Nanoscale 6, 5172-5180 published Jul. 2, 2014.

Moitra, P., Kumar, K., Kondaiah, P. & Bhattacharya, S. Efficacious Anticancer Drug Delivery Mediated by a pH-Sensitive Self-Assembly of a Conserved Tripeptide Derived from Tyrosine Kinase NGF Receptor. Angew. Chem. Int. Ed. 53, 1113-1117 published Nov. 12, 2013.

\* cited by examiner

FIG. 2A
FIG. 2B
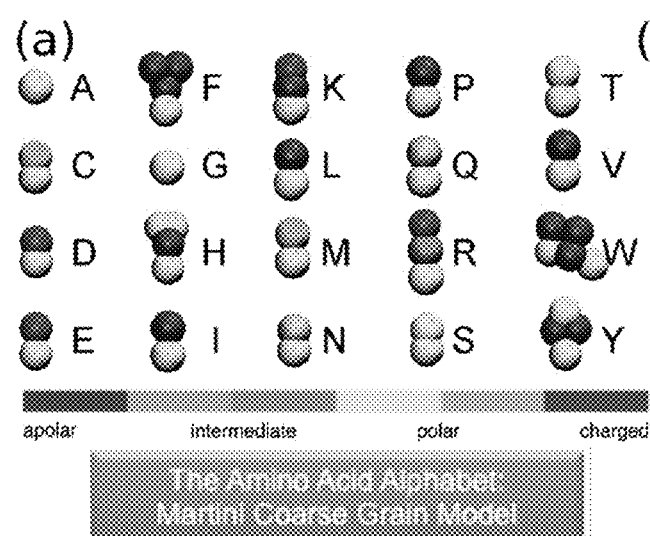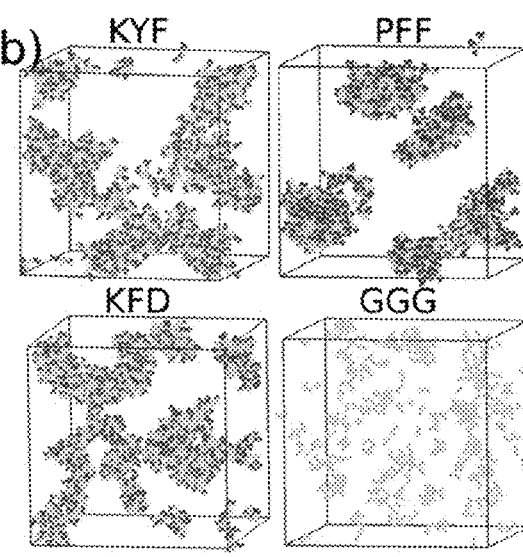
FIG. 2C
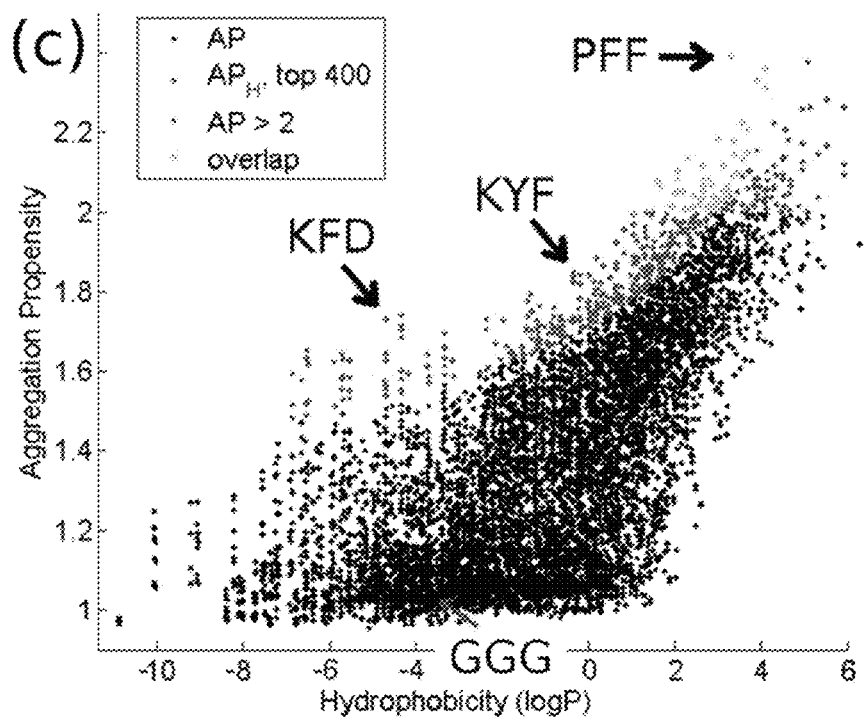

Figure 5

Table 2.

Literature

| Tripeptide | VFF | FFF | LFF | CFF | FFV | VYV | KFG | DFN | ECG |
|---|---|---|---|---|---|---|---|---|---|
| Ref. | 10 | 9,31,42 | 11 | 8 | 10 | 13 | 14 | 15 | 41 |
| Assembly observed? | Yes | Yes | Yes | Yes | Yes | Yes | Yes | No | No |
| AP 50 ns (nr)[b] | 2.33 (4) | 2.26 (7) | 2.07 (58) | 2.05 (69) | 2.03 (89) | 1.88 (377) | 1.56 (737) | 1.17 (4720) | 1.01 (7590) |
| # AP$_H$[b] | 158 | 2422 | 2390 | 703 | 1319 | 223 | 2001 | 4867 | 7660 |
| Structure | | | | | | | | | |

This work

| Tripeptide | PFF | FYI | FHF | YFI | KFF |
|---|---|---|---|---|---|
| D (10$^{-10}$ m$^2$/s)[c] | N.S. | N.S. | N.S. | 3.8 | 3.8 |
| AP 50 ns (nr)[b] | 2.39 (1) | 2.22 (10) | 2.09 (44) | 1.97 (190) | 1.92 (264) |
| # AP$_H$[b] | 4 | 107 | 301 | 1041 | 30 |
| Structure | | | | | |

| Tripeptide | IYF | KYF | RYF | KYY | KYW |
|---|---|---|---|---|---|
| D (10$^{-10}$ m$^2$/s)[c] | N.S | 3.7 | 3.8 | 3.7 | 3.7 |
| AP 50 ns (nr)[b] | 1.89 (347) | 1.85 (478) | 1.80 (648) | 1.79 (662) | 1.78 (728) |
| # AP$_H$[b] | 1572 | 28 | 212 | 23 | 146 |
| Structure | | | | | |

| Tripeptide | FYK | KFD | KHD | KLL | GGG |
|---|---|---|---|---|---|
| D (10$^{-10}$ m$^2$/s)[c] | 3.9 | 4.0 | 4.5 | 3.9 | 6.3 |
| AP 50 ns (nr)[b] | 1.73 (941) | 1.73 (959) | 1.63 (1480) | 1.31 (3751) | 1.07 (6276) |
| # AP$_H$[b] | 267 | 1 | 7 | 3918 | 6095 |
| Structure | | | | | |

Top scoring peptides

| # | AP score | AP$_H$ score |
|---|---|---|
| 1 | PFF | KFD |
| 2 | WFL | KWD |
| 3 | MFF | HKD |
| 4 | VFF | PFF |
| 5 | FFM | KWE |
| 6 | FWF | WKE |
| 7 | FFF | KHD |
| 8 | WWF | PCF |
| 9 | FWI | KWF |
| 10 | FYI | KFW |
| 11 | VFW | KHE |
| 12 | PWF | TSF |
| 13 | IFF | SCW |
| 14 | LCF | WKD |
| 15 | WLL | KYD |
| 16 | SFW | KEH |
| 17 | IFW | GFF |
| 18 | WFF | VAW |
| 19 | FFW | SSF |
| 20 | IMW | KYE |

[a]: in the presence of HFIP. [b]: ranking out of 8000, [c]: Diffusion constant as determined by DOSY.

SELF-ASSEMBLING TRIPEPTIDES

FIELD OF THE INVENTION

The present invention relates to a method of predicting the propensity of tripeptides to from aggregates in solution. The present invention also provides tripeptides which are able to form aggregates in solution, as well as uses thereof. The present invention also provides nanostructures formed by self-aggregation of tripeptides of the present invention. The present invention also provides pH responsive aggregates as well as methods of screening for the ability of a tripeptide to form a pH dependent aggregate or gel.

BACKGROUND OF THE INVENTION

Peptides with the ability to spontaneously assemble into nanostructures of defined size, shape and chemical functionality are of tremendous interest, with potential biological, medical, electronic, photonic and nanotechnology applications. The enormous chemical sequence space which is available from 20 amino acids likely harbours many interesting candidates, including gelators, but it is currently not possible to predict supramolecular behaviour from sequence alone. Even for very short sequences (e.g. tripeptides), existing examples have been serendipitously discovered and largely limited to hydrophobic sequences, which form (nanoscale) aggregates, but lack the amphiphilicity required to gelate.

The use of very short peptides, pioneered by Gazit,[5] is especially attractive, enhancing opportunities for rational design combined with robustness, scalability and cost reduction. Two main challenges are currently limiting the expansion of this field. Most examples of short peptides (<5 amino acids) that have been discovered since diphenylalanine (FF)[5] contain only hydrophobic amino acids (vide infra). This is no surprise as hydrophobic interactions dominate self-assembly in water but it also limits their aqueous solubility and restricts applications. Secondly, in spite of two decades of intensive research since the first examples of short self-assembling peptides,[6,7] most examples have been either discovered by serendipity or by mapping onto known sequence design rules from biological systems.[3,4]

Experimentally, a small set of tripeptides has been reported to assemble into nanostructures in (mainly) aqueous environments, e.g. CFF forms nanospheres, FFF forms fibrous and plate-like assemblies;[8,9] VFF, FFV and LFF form heterogeneous nanostructures;10-12 micelle formation was discovered in VYV[13] and KFG,[14] which in the latter case could reversibly be converted to nanotubes by lowering the pH; disordered aggregates were found upon drying of a solution of DFN.[15] One common approach to alter the self-assembly properties of short peptides is protection of the terminal amine or acid groups, with acetyl,[16,17] t-butyloxycarbonyl[20,21] or large aromatic groups,[18,19,22,23] reducing charge repulsions and introducing w-stacking/hydrophobic contributions to favour self-assembly and gelation. Simple rules have been described for assembling peptides based on repeating sequences based on biological systems.[24,25] However, gelators based on unprotected tripeptides are still elusive and only a small section of the available sequence space has been explored.

A number of researchers have recently studied molecular self-assembly in a supramolecular materials context using computational approaches.[26,27] In previous work, we have shown that the propensity of dipeptides (two amino acids) to aggregate can be predicted using coarse-grain (CG) Molecular Dynamics (MD).[28] Several other studies comprising short peptide fragments of biological relevance, such as NFGAIL[16,29] (a fragment of human islet amyloid polypeptide) or FF,[28,30] FFF[31] and KLVFFAE[32] (parts of amyloid $\beta_{16-22}$), have shown the usefulness of CG-MD for studying peptide self-assembly. However, in all of these cases, the focus was on systems that were experimentally known to self-assemble, i.e. these examples are not predictive in nature.

Our earlier work was directed to the virtual screening of dipeptide aggregation and this allows virtual screening of all 400 dipeptides combinations. However, the ability of such a technique to screen tripeptides (8,000 in total) or larger peptides for their propensity to aggregate was not considered. As there are 8,000 tripeptides, it is impractical to synthesise and test all possible combinations for their ability to aggregate and it would be desirable to develop a virtual screening method to assist with this.

The present invention is based on an improved virtual screening method which allows all 8000 tripeptide sequences to be studied in a virtual manner and their propensity for aggregation to be estimated such that classes of peptides, such as tripeptides with certain properties that renders them most likely to form aggregates may be identified.

The screening method may be expanded to take account of how other parameters, such a pH, may affect peptide aggregation. A further aspect of the invention are the classes of peptides thus discovered themselves, as they show surprising, unprecedented and useful self-assembly behaviour, including gelation.

It is amongst the objects of the present invention to provide a method of virtual screening of peptides, such as tripeptides for their propensity to form aggregates in solution and optionally at a particular pH.

SUMMARY OF THE INVENTION

The present invention is based on the development of an improved method of virtual screening for the propensity of peptides to form aggregates in solution and is based on the discovery of classes of tripeptides thus discovered which display unusual self-assembly behaviours.

In one aspect there is provided a method of identifying a peptide for aggregation in aqueous, (such as pH neutral e.g. pH 6.8-7.2 especially pH7, although acidic pH such as between pH3-5 and alkali pH, such as pH 9-12, may be appropriate in some circumstances) solution, the method comprising identifying a peptide by determining a hydrophilicity-adjusted measure of propensity for aggregation ($AP_H$) for the peptide, the $AP_H$ being determined by adjusting a measure of propensity of aggregation (AP) for the peptide in dependence on a measure of hydrophilicity for the peptide.

By adjusting the AP in dependence on a measure of hydrophilicity, an improved measure of propensity for aggregation may be obtained. $AP_H$ may be used to provide a method of virtual screening of peptides for their propensity to form aggregates in solution.

The peptide may comprise a tripeptide, tetrapeptide, pentapeptide or even larger peptide. Preferably the peptide is a tripeptide.

The identifying of the peptide may comprise determining whether the determined $AP_H$ for the peptide meets or exceeds a threshold value for $AP_H$.

A threshold value may be determined for $AP_H$, with peptides having a value of $AP_H$ meeting or exceeding the threshold being considered to have a high propensity for aggregation. Peptides with a high propensity for aggregation may be selected for particular applications. Peptides with a high propensity for aggregation may be selected to be synthesised.

The peptide is one of a plurality of peptides, and the identifying of the peptide comprises determining an $AP_H$ for each of the plurality of peptides and identifying at least one of the plurality of peptides in dependence on the determined $AP_H$ for the plurality of peptides.

The plurality of peptides may comprise a plurality of peptides, such as a plurality of tripeptides. The plurality of peptides comprises substantially all possible combination of peptides encoded by naturally occurring amino acids. For example, for tripeptides there are 8000 peptides ($20^3$ where 20 is the number of naturally occurring amino acids). The approach can conceptually be expanded to include non-natural amino acids, such as Citrulline, norvaline, etc., and N- and C-terminal protected amino acids.

A method for virtually screening peptides (for example, tripeptides) may comprise screening large numbers of peptides by calculating $AP_H$ for each peptide, and identifying peptides based on the calculated $AP_H$. Identification of peptides by $AP_H$ may, in some circumstances, provide more promising candidates for aggregation than identification by AP alone.

Identifying at least one of the plurality of peptides in dependence on the determined $AP_H$ for the plurality of peptides may comprise identifying a subset of the plurality of peptides, the subset comprising the peptides having the highest $AP_H$.

The subset of the plurality of peptides may comprise the 100 peptides having the highest $AP_H$, optionally the 200 peptides having the highest $AP_H$, further optionally the 400 peptides having the highest $AP_H$.

The subset of the plurality of peptides may comprise 10% of the plurality of peptides having the highest $AP_H$, optionally the 5% of the plurality of peptides having the highest $AP_H$, further optionally the 2% of the plurality of peptides having the highest $AP_H$.

The number of peptides identified by $AP_H$ from the plurality of peptides may depend on the number of peptides in the plurality. For example, from the 8,000 possible tripeptides, a subset of 400 peptides (5% of all peptides) may be selected.

Identifying the subset of the plurality of peptides may comprise identifying all peptides in the plurality of peptides having an $AP_H$ greater than a threshold value for $AP_H$, or greater than or equal to a threshold value for $AP_H$.

The threshold value may be determined by calculating the $AP_H$ for each peptide in the plurality of peptides and setting the threshold value to deliver a desired size of subset. The threshold value may be determined based on knowledge of the $AP_H$ of peptides that have successfully aggregated.

The method may further comprise obtaining the AP for the peptide from simulation. Obtaining the AP for the peptide from simulation comprises performing a molecular dynamics simulation for the peptide.

Where there are a plurality of peptides, the method may comprise obtaining the AP for each of the plurality of peptides from a respective simulation, which may comprise a molecular dynamics simulation.

The AP for the peptide may comprise a ratio between a solvent accessible surface area at the beginning of the molecular dynamics simulation and a solvent accessible surface area at the end of the molecular dynamics simulation.

The measure of hydrophilicity may comprise a sum of Wimley-White whole-residue hydrophobicities for amino acids in the peptide or any similar hydrophobicity scale (such as the Kyte and DooLittle scale [Kyte J, Doolittle R F. *J Mol Biol*. 1982 May 5; 157(1):105-32.], or the Hessa and Heijne scale[Hessa T, Kim H, Bihlmaier K, Lundin C, Boekel J, Andersson H, Nilsson I, White S H, von Heijne G. *Nature*. 2005 Jan. 27; 433(7024):377-81]) that relates the hydrophobicity of amino acids to rank the relative hydrophobicity/hydrophilicity of the peptide.

Adjusting the AP for the peptide in dependence on a measure of hydrophilicity for that peptide may comprise raising the AP to a power and multiplying by the measure of hydrophilicity.

At least one of the AP and the measure of hydrophilicity may be normalised prior to the adjusting of the AP in dependence on the measure of hydrophilicity.

Determining $AP_H$ for the peptide may comprise using the equation: $AP_H = (AP')^\alpha (\log P)'$ wherein $\alpha$ is a numerical constant, log P is the measure of hydrophilicity for the peptide, and an apostrophe denotes normalisation. $\alpha$ may have a value between 0.5 and 5, optionally between 1 and 4, further optionally between 1 and 3.

Changing the value of a in the above equation may change the relative weighting between the AP and the measure of hydrophilicity. Where a value for $AP_H$, for example a threshold value for $AP_H$, is determined, the value for $AP_H$ may be dependent on the value for $\alpha$.

The above described methods may be further modified to take account of the measure of protonation of each amino acid individually and/or when part of a particular peptide sequence, such as a tripeptide. The amino and carboxy termini of peptides, as well as certain exposed amino acid side chains are capable switching between protonated and deprotonated forms, depending on the pH of the surroundings and the inventors have observed that peptide aggregation or gelation can be affected by changes in pH. Therefore, screening for the ability of tripeptides to aggregate within different pH environments can be achieved by modifying the standard coarse-grained beads, which are parameterized for neutral pH, to represent the sidechains in the alternative protonation state. For example, rather than utilising a protonated N-terminus beads ($NH_3^+$) a neutral N-terminus bead ($NH_2$) bead could be used to examine the effect of moving above pH 10, whereby the N-terminus would be deprotonated.

In a further aspect there is provided a method of producing a peptide capable of self-aggregation in solution, the method comprising identifying a peptide by determining a hydrophilicity-adjusted measure of propensity for aggregation ($AP_H$) for the peptide, the $AP_H$ being determined by adjusting a measure of propensity of aggregation (AP) for the peptide in dependence on a measure of hydrophilicity for the peptide and synthesising the peptide.

The peptide may be one of a plurality of peptides, and the identifying of the peptide may comprise determining an $AP_H$ for each of the plurality of peptides and identifying at least one of the plurality of peptides in dependence on the determined $AP_H$ for the plurality of peptides.

The method may further comprise determining the protonation state of a peptide at a desired pH in order to predict whether or not the peptide will be expected to aggregate and optionally form a gel at the particular pH. The method may further comprise providing a solution at the particular pH and allowing the peptide to aggregate and optionally form a nanostructure or gel at the particular pH. This may allow a further agent, such as a drug molecule, protein or enzyme, for example, to be trapped upon peptide aggregation.

The inventors have observed that by altering the pH the aggregated peptides may disaggregate. In this manner any trapped agent, such as a drug may be released upon peptide disaggregation. Alternatively, the trapped agent may be released slowly by degradation or dissolution of the nanostructure without alteration of pH.

Thus, in a further aspect there is provided a pH responsive peptide as described herein, such as a tripeptide, for use in entrapping an agent, such as a drug molecule, upon peptide aggregation and releasing the agent upon peptide disaggregation. The pH responsive peptide is capable of forming an aggregate at a first pH or pH range and does not aggregate or disaggregates at a second pH or pH range.

In accordance with the present invention and in view of the peptides which can be prepared, it is possible to provide peptides which are capable of aggregating/disaggregating at a particular desired pH or pH ranges.

In a further aspect there is provided a pH responsive peptide aggregate comprising a peptide or peptides as described herein and an agent entrapped, complexed or otherwise associated with the aggregated peptide.

In a further aspect there is provided a method a delivering an agent to a particular location in a body, or not in a human or animal body, for example, the method comprising providing a pH responsive peptide aggregate comprising a peptide or peptides as described herein and an agent entrapped, complexed or otherwise associated with the aggregated peptide and releasing the agent by altering the pH so as to disaggregate the peptide. Altering the pH may be a natural consequence of the aggregated peptide being transported to a site or location of altered pH, for example.

In some embodiments, the agent is a pharmaceutical agent, such as a small molecule (e.g. less than 500 Daltons), or is a nucleic acid. In some embodiments, the nucleic acid is an antisense oligonucleotide, aptamer or interfering RNA (RNAi). In some embodiments, the nucleic acid is a microRNA (miRNA), shRNA or siRNA. In further embodiments, one or more of the pharmaceutical agents are a protein or peptide. In some embodiments, the protein is an antibody. In some embodiments, one or more of the pharmaceutical agents are a hydrophobic agent or a hydrophilic agent (e.g., a hydrophobic drug or hydrophilic drug, respectively). In some embodiments, the one or more of the pharmaceutical agents are a hydrophobic agent and a hydrophilic agent (e.g., a hydrophobic drug and/or a hydrophilic drug). In some embodiments, one or more pharmaceutical agents are released from the peptide aggregate when the particle is in a cell or other desired location (e.g., within the endosome or at the site of a tumor).

The use of pH-responsive polymers in drug delivery is known in the art and the skilled addressee is directed to Schmalijohann (Advanced Drug Delivery Reviews 58 (2006), p 1655-1670) for some background and teaching in this regard. pH responsive drug delivery may find particular application in delivering hydrophobic agents which may be difficult to administer and/or allow targeted delivery of an agent to a particular location in the body or in a cell, which has a pH which causes disaggregation of the peptide and release of an entrapped agent. The present peptides may also enable acid sensitive agents to be administered orally, for example. Thus, a formulation may be provided with an aggregated peptide comprising an entrapped acid sensitive agent. After passing low pH compartments of the gastrointestinal tract, the aggregated peptide encounters regions of higher pH, which causes the peptide to disaggregate and release the acid sensitive agent.

In a further aspect there is provided a method of producing a nanostructure comprising a peptide capable of self-aggregation in solution, the method comprising identifying a peptide by determining a hydrophilicity-adjusted measure of propensity for aggregation ($AP_H$) for the peptide, the $AP_H$ being determined by adjusting a measure of propensity of aggregation (AP) for the peptide in dependence on a measure of hydrophilicity for the peptide, synthesising the peptide, and allowing the peptide to aggregate.

The peptide may be provided in a solution where the pH is such that peptide aggregation is capable of occurring.

The peptide may be one of a plurality of peptides, and the identifying of the peptide may comprise determining an $AP_H$ for each of the plurality of peptides and identifying at least one of the plurality of peptides in dependence on the determined $AP_H$ for the plurality of peptides.

By observing the sequence of thus identified peptides, classes of peptides with certain self-assembly behaviours may be identified, for example those which contain for example, aromatic, anionic, cationic, H-bonding residues in certain positions.

In a further aspect there is a provided a peptide or nanostructure obtainable by any of the above methods.

Typically the peptides of the present invention may aggregate at a concentration of between 1-500 nM, such as 10-200 nM, 15-100 nM, or 20-60 nM.

In a further aspect there is provided a solution comprising a self-aggregated tripeptide, , the tripeptide having the formula:

wherein
$A_1$ is a hydrogen bond donating amino acid, such as K, R, S, T, or P, H, or W, or F;
$A_2$ is an aromatic amino acid, such as F, Y, W, or H;
$A_3$ is an aromatic amino acid, such as F, Y, or W, or a negatively charged amino acid such as D or E.

In a further embodiment there is provided a solution comprising a self-aggregated tripeptide, the tripeptide having, the tripeptide having the formula:

wherein
$A_1$ is K, R, S, T or P;
$A_2$ is F, Y, or W;
$A_3$ is F, Y, W, D or E.

In a further aspect there is provided a solution comprising a self-aggregated tripeptide as identified in Table 2. Preferably the peptide displays an $AP_H$ value of >0.10, 0.11, 0.12, 0.13, 0.14, 0.15, 0.16, 0.17, or 0.18. Preferably the tripeptide displays an AP value of <2.0. Preferred tripeptides which are capable of self-aggregating and/or forming gels are KYF, KFF, KYW, KYY and FFD. It should be understood that the tripeptides of the present invention exclude the peptides CFF, FFF, VFF, FFV, LFF, VYV, KFG or DFN.

In a further aspect there is provided an aggregate or nanostructure formed by self-aggregating a tripeptide (such as KYF, KFF, KYW, KYY, or FFD) as defined herein with the proviso that the tripeptide is not CFF, FFF, VFF, FFV, LFF, VYV, KFG or DFN.

Typically the aggregates or nanostructures are formed or capable of being formed in solution. The solution is typically an aqueous solution such as water or saline, but can be any suitable aqueous solution. Alternatively the solution may be a non-aqueous such as a solvent solution, for example an alcohol such as methanol, ethanol or octanol, or other suitable solvent. Peptide aggregation may also be included and/or facilitated by changing solution/solvent conditions such as by altering salt concentration, pH, (e.g. between pH 3-10, such as pH 5-8) temperature or any other suitable physiological condition.

Thus, if a further embodiment, there is provided a method of forming a self-assembled tripeptide aggregate, the tripeptide having the formula:

$$A_1\text{-}A_2\text{-}A_3$$

wherein
$A_1$ is a hydrogen bond donating amino acid, such as K, R, S, T, or P, H, or W, or F;
$A_2$ is an aromatic amino acid, such as F, Y, W, or H;
$A_3$ is an aromatic amino acid, such as F, Y, or W, or a negatively charged amino acid such as D or E, or
the tripeptide having the formula:

$$A_1\text{-}A_2\text{-}A_3$$

wherein
$A_1$ is K, R, S, T or P;
$A_2$ is F, Y, or W;
$A_3$ is F, Y, W, D or E,
the method comprising providing a solution comprising the tripeptide as defined above and changing solution/solvent conditions such as by altering salt concentration, pH, (e.g. between pH 3-10, such as pH 5-8) temperature or any other suitable physiological condition in order to facilitate self-aggregation of the tripeptide to occur.

The peptide aggregate or nanostructure may further comprise an entrapped, bound or otherwise associated agent as described hereinabove. Such agents may be administered to a subject by any suitable route, such as and may be released from the aggregate following natural degradation, enzymic action and/or pH change, for example.

Thus, in a further aspect there is provided a formulation, such as a pharmaceutical formulation comprising a peptide aggregate or nanostructure in accordance with the present invention, the peptide aggregate or nanostructure comprising an entrapped, bound or otherwise associated agent, such as pharmaceutically active agent, optionally with a pharmaceutically or physiologically acceptable excipient.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association the peptide aggregate or nanostructure comprising an entrapped, bound or otherwise associated agent with liquid carriers or finely divided solid carriers or both and then, if necessary, shaping the product into the desired formulation.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient

DETAILED DESCRIPTION OF THE INVENTION

The present invention will now be further described by way of example and with reference to the figures which show:

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 (Cont): shows AP as a function of hydrophilicity for all 8000 tripeptides. Green dots represent the top 400 tripeptides from the hydrophobicity-corrected APH score with alternative values for coefficient $\alpha$. (d) $\alpha=1$, (e) $\alpha=3$.

FIG. 5 shows Table 2: Aggregation Propensity and structural results from CG MD simulations. Top half: comparison of MD results with tripeptides studied in literature, bottom half: tripeptides experimentally studied in this work.

Figure 1A:
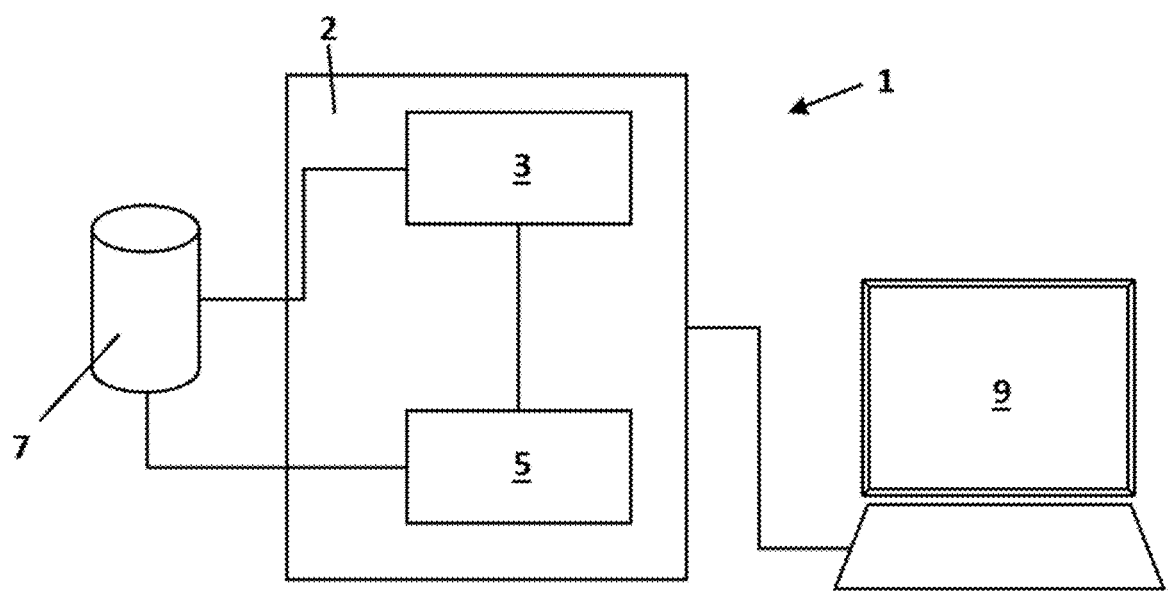
FIG. 1(a) is a schematic diagram of a computing apparatus in accordance with an embodiment.

The FIG. 1(a) is a system for use in identifying peptides, in accordance with the invention. The system includes a simulation unit 3 and a peptide identification unit 5. In the present embodiment, the system 1 comprises a high-performance computer system. In other embodiments, the computing apparatus may comprise any appropriate computing apparatus or combination of computer apparatuses, for example a PC, a workstation, a mainframe, or a network comprising multiple computer apparatuses.

The simulation unit 3 is operable to perform a molecular simulation of aggregation for each of a plurality of peptides to determine a measure of propensity for aggregation for each of the peptides.

The peptide identification unit 5 is operable to adjust the measure of propensity for aggregation for each peptide in dependence on a measure of hydrophilicity for the peptide, and to identify at least one peptide in dependence on the hydrophilicity-adjusted aggregation propensity.

The system 1 may have a user interface 9 (e.g. a keyboard and/or other user input device, one or more screens), a data store 7 in the form of one or more volatile and/or non-volatile data storage devices (e.g. a hard drive, RAM), functioning as a data store, and a processor 2, functioning as the processing resource.

In the present embodiment, the simulation unit and peptide identification unit are each implemented in the processor 2 by means of a computer program having computer-readable instructions that are executable to perform the method of the embodiment, However, in other embodiments, the units may be implemented in software, hardware, or any suitable combination of software and hardware. Although particular units are described in this embodiment, in alternative embodiments functionality of one or more of these units can be provided by a single unit, processing resource or other component, or functionality provided by a single unit can be provided by two or more units or other components in combination.

Figure 1B:
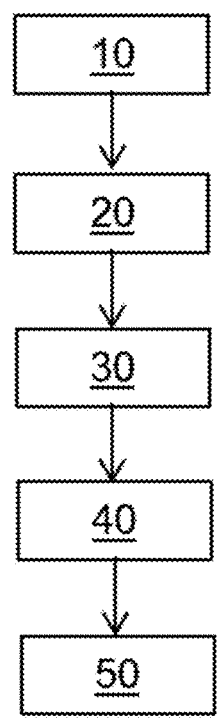
FIG. 1(b) is a flow diagram illustrating a workflow in accordance with an embodiment.

In use, the system 1 functions according to the generalised work flow set out in FIG. 1(b). It will be appreciated by the skilled addressee that the sequence of steps may vary from the sequence set out in FIG. 1(b) and described herein.

At stage 10, the simulation unit 3 performs a molecular dynamics simulation of each of a plurality of peptides. In some embodiments, the molecular dynamics simulation is performed using GROMACS with the MARTINI force field—Gromacs is a software package for running molecular dynamics simulations [http://www.gromacs.org/About_Gromacs]. In other embodiments, any suitable molecular dynamics method may be used. For each peptide, the simulation unit 3 determines a solvent accessible surface area at the start of the molecular dynamics simulation ($SASA_{initial}$) and a solvent accessible surface area at the end of the molecular dynamics simulation ($SASA_{final}$). In some embodiments, the determination of SASA is performed using Visual Molecular Dynamics (VMD). In other embodiments, any suitable program for determining SASA may be used, many different programs can be used to calculate the SASA, such as NACCESS—www.bioinf.manchester.ac.uk/naccess/, pymol, etc.]. The simulation unit 3 determines a measure of propensity for aggregation (AP) for each peptide from the determined $SASA_{initial}$ and $SASA_{final}$ using equation 1.

At stage 20, the peptide identification unit 5 calculates a hydrophilicity-adjusted measure of propensity for aggregation ($AP_H$) for each peptide. For each peptide, the peptide identification unit 5 retrieves from data store 7 a measure of hydrophilicity for the peptide. The peptide identification unit 5 uses the AP determined at stage 10 and the retrieved measure of hydrophilicity to calculate $AP_H$ using equation 2. Equation 2 is an empirically founded equation.

$$AP_H = (AP')^\alpha \cdot \log P' \quad (2)$$

where log P is the measure of hydrophilicity and where the apostrophe indicates the normalization of the respective variable between 0 and 1. The normalisation is determined by scaling all values relative to the range covered by the set of peptides using the following equation:

$$AP_H = \left(\frac{AP(\text{trip}) - AP_{min}}{AP_{max} - AP_{min}}\right)^\alpha \cdot \left(\frac{\log P(\text{trip}) - \log P_{min}}{\log P_{max} - \log P_{min}}\right)$$

Figure 2D:
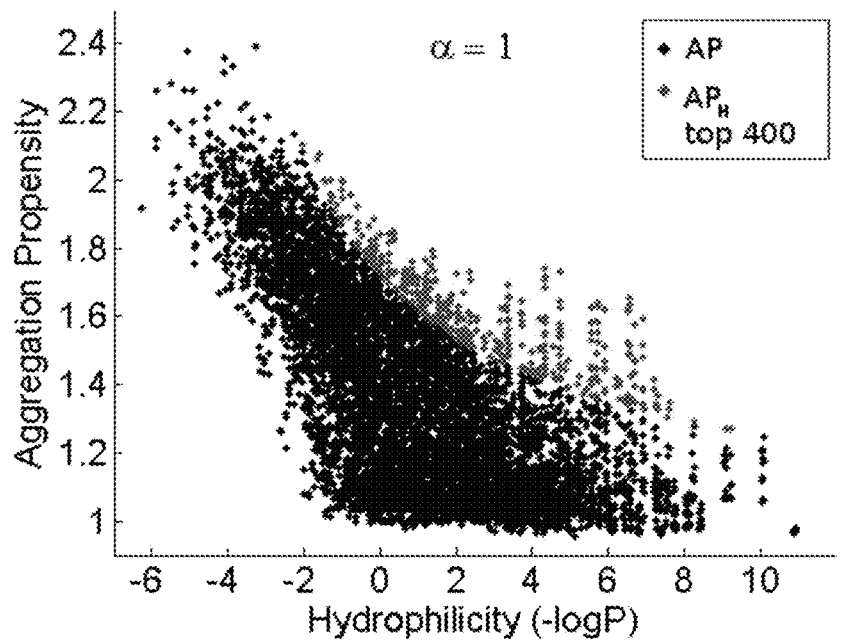
FIG. 2: shows screening for self-assembling tripeptides. (a) Representation of all 20 gene-encoded amino acids in the MARTINI force field. Different colours represent different types of beads, as indicated by the legend. Image adapted with permission from ref. 33. Copyright 2008 American Chemical Society. (b) 50 ns MD simulation results of GGG, PFF, KFD and KYF tripeptides, showing various levels of aggregation. (c) Aggregation Propensity as a function of hydrophobicity for all 8000 tripeptides. Red diamonds represent all tripeptides with AP>2. Green diamonds represent the top 400 tripeptides from the APH score ($AP_H=AP^\alpha\cdot\log P$, $\alpha=2$) with the overlapping candidates shown in orange. The arrows point to the data points for GGG, PFF, KFD and KYF.

In equation 2, α is an arbitrary coefficient that can be used to determine the weight of the normalized AP score to the $AP_H$ value. In this embodiment, α=2 was used to give a compromise between AP and hydrophilicity. Depending on the desired properties, the exponent can be decreased (increased) to include more (less) hydrophilic peptides. For a selection with α=1 and α=3 see FIGS. 2(d) and (e).

Any appropriate measure of hydrophilicity may be used, in particular those that relate the hydrophobicity of amino acids to rank the relative hydrophobicity/hydrophilicty of the peptide.

At stage 30, the peptide identification unit 5 identifies a subset of the plurality of peptides based on the determined $AP_H$ values. In some embodiments, the peptide identification unit 5 identifies a subset by determining the size of the desired subset, ranking the peptides in order of $AP_H$, and choosing the appropriate number of peptides. For example the peptide identification unit 5 identifies the top 200 peptides in order of $AP_H$. The peptide identification unit 5 may choose the size of the subset to be a proportion of the entire set of peptides under consideration, for example the top 10% of peptides in order of $AP_H$.

In other embodiments, the peptide identification unit 5 determines a threshold value of $AP_H$. In some embodiments, the threshold value of $AP_H$ is determined from the determined values of $AP_H$ for the peptides, for example by setting a threshold that separates the top 10% of peptides from the remaining peptides. In other embodiments, the threshold value of $AP_H$ may be set by another method, for example by using the determined $AP_H$ of peptides that are already known to have good aggregation properties. In some embodiments, the threshold value of $AP_H$ may be set by a user. The peptide identification unit 5 may identify a subset by identifying all peptides with an $AP_H$ that meets or exceeds the threshold value.

At stage 40, at least one of the subset of peptides is synthesised using methods described below. At stage 50, the synthesised peptide is allowed to aggregate, for example to form a nanostructure.

Although the above embodiments described the identification of a subset of peptides in a plurality of peptides, in other embodiments only one peptide is used in the method of the flowchart of FIG. 1(b), with a single determination of $AP_H$ being performed. In such embodiments, a threshold $AP_H$ may be used at stage 30 and the peptide may be identified as potentially suitable for aggregation in solution if its $AP_H$ value exceeds the threshold value.

Experimental Section

In an experiment, simulations were performed for all 8000 tripeptides. Tripeptide coordinate files were created using VMD scripting tools[1*] and converted to CG representation in the MARTINI force field (version 2.2) using martinize.py with flag -ss =EEE.[2] Using the GROMACS code version 4.5.3,3 a cubic box of 13×13×13 nm³ containing 300 zwitterionic tripeptides was created giving a peptide concentration of 0.23 mol L⁻¹ in standard CG water, with side chains in their most prevalent charge state at pH 7. Note that the computational concentration is one order of magnitude higher than the experimental one to accelerate the assembly process and thus decrease computational cost. Periodic boundary conditions were used. The box was energy minimized for 5000 steps or until forces on atoms converged to under 200 N. The minimized box was subsequently equilibrated for 500,000 steps of 25 fs, using the Berendsen algorithms[4] to keep temperature (τT=1 ps) and pressure (τP=3 ps) around 303 K and 1 bar, respectively. Bond lengths in aromatic side chains and the backbone-side chain bonds in I, V and Y were constrained using the LINCS algorithm.[5] The total simulation for this initial screening phase equates 12.5 ns, but this equates to roughly 50 ns 'effective time', due to the smoothness of the CG potentials.[6,7] All times reported in this paper take into account this speedup factor. For the tripeptides selected for further study, the water in the solvated energy-minimized box was converted to polarizable water (PW)[8] to better account for charge screening. This system was then energy-minimized again and run in the NPT ensemble for 4.106 steps, or 400 ns effective time. Finally, for the systems with experimental information available, a similar, but larger simulation was carried out for 1200 ns using 1200 peptides in a box of 24×24×24 nm³ (peptide concentration 0.14 M in standard CG water) to allow the formation of larger structural features like tubes, spheres or fibers where appropriate.

The measure of hydrophilicity for a given tripeptide may be written as log P(trip). Since log P(trip) is a unitless number linearly proportional to ΔGwater-oct (see SI) and is normalized in Eq. 1, it was chosen to define it simply as the sum of the Wimley-White whole-residue hydrophobicities[37,38] $\Delta G_{water\text{-}octanol}$ (kcal/mol) for the tripeptide, given by:

$$\log P = \Sigma_{i=1}^{3} \Delta G_{water\text{-}octanol} \quad (3)$$

Explanation of relationship of hydrophobicity "log P" and $\Delta G_{water\text{-}octanol}$ Considering the Equilibrium

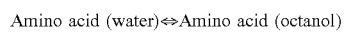

Amino acid (water) ⇌ Amino acid (octanol)

An equilibrium constant $K_{eq}$, in this case defined as the partition coefficient P can be written up as $$K_{eq} = \frac{[\text{Amino-acid}]_{oct}}{[\text{Amino-acid}]_{wat}} \equiv P,$$

In chemical equilibrium, the standard Gibbs free energy change ΔG° can be written as $$\Delta G° = -RT \ln K_{eq}$$

Showing that the standard free energy change is linearly proportional to the logarithm of P $$\Delta G° = \frac{-RT}{\log e} \log P$$

$AP_H$ values were calculated for all 8000 tripeptides from 50 ns simulations. A subset of tripeptides was chosen based on the calculated $AP_H$ values, which comprised the 400 tripeptides having the highest $AP_H$ values. An extended molecular dynamics simulation was performed on each of the subset of tripeptides. Computational power allowed only the top 400 scoring peptides indicated after 50 ns by this protocol to be used in extended simulations. A number of the top scoring peptides were synthesised.

Peptide Synthesis

GGG was purchased from Sigma Aldrich. All other tripeptides were synthesised using standard Fmoc solid phase peptide synthesis with HBTU activation. Briefly, Fmoc Wang resin loaded with the first amino acid was allowed to swell in DMF for 15 min (repeated twice). Fmoc deprotection was performed in 20% piperidine in DMF (repeated twice, for 5 min and 15 min). HBTU activation was performed with 3 eq. of Fmoc-amino acid and 3 eq. of HBTU in DMF (5 ml for every gram of resin), with 6 eq. DIPEA. Coupling was performed at RT for 3 h, after thorough washes with DMF and DCM. Final cleavage was obtained using a mixture of TFA/TIPS/water (95:2.5:2.5). The process was repeated to couple the third amino acid. Resulting peptides were allowed to be precipitated in cold ether or lyophilized when appropriate. The precipitated peptides were allowed to dry under vacuum overnight. The purity of each peptide was verified by HPLC. The peptides' identity was verified by ESI-MS and ¹H NMR.

HPLC

A 30 µl sample was injected onto a Macherey-Nagel C18 column (Intersil Phenyl for KFD and KHD) with a length of 250 mm and an internal diameter of 4.6 mm and 5-mm fused silica particles at a flow rate of 1 ml/min. The eluting solvent system (in all cases with 0.1% v/v TFA added) had a linear gradient of 20% (v/v) acetonitrile in water for 4 min, gradually rising to 80% (v/v) acetonitrile in water at 35 min. This concentration was kept constant until 40 min when the gradient was decreased to 20% (v/v) acetonitrile in water at 42 min. The purity of each peak was determined by UV detection at 214 nm.

FTIR

Samples were contained in a standard IR transmission cell (Harrick Scientific) between two 2 mm CaF2 windows, separated by a polytetrafluoroethylene (PFTE) spacer of 50 µm thickness. Spectra were recorded on a Bruker Vertex 70 spectrometer by averaging 25 scans at a spectral resolution of 1 cm⁻¹. Spectra were corrected for absorption from a phosphate buffer blank sample and absorptions from trifluoroacetic acid (TFA).

TEM

Carbon-coated copper grids (200 mesh) were glow discharged in air for 30 s. The support film was touched onto the gel surface for 3 s and blotted down using filter paper. Negative stain (20 ml, 1% aqueous methylamine vanadate (Nanovan; Nanoprobes) was applied and the mixture was blotted again using filter paper to remove excess. The dried specimens were then imaged using a LEO 912 energy filtering transmission electron microscope operating at 120 kV fitted with 14 bit/2 K Proscan CCD camera Diffusion Ordered NMR Spectroscopy (DOSY NMR)

Peptide solutions were prepared in $D_2O$ at 10 mM peptide concentration as a compromise between solubility and NMR signal intensity. DOSY spectra were acquired at 600 MHz using a Bruker Avance 600 spectrometer using the Bruker microprogram dstebpgp3sat at 298 K. The eddy current delay (Te) was set to 5 ms. The diffusion time was adjusted to 100 ms. The duration of the pulse field gradient, Ag, was optimized in order to obtain 5% residual signal with the maximum gradient strength with the resulting A value of 3.6 ms. The pulse gradient was increased from 2 to 95% of the maximum gradient strength using a linear ramp 16 k data points in the F2 dimension (20 ppm) and 16 data points in the F1 dimension were collected. Final data sizes were 16 k×128.

Dynamic Light Scattering (DLS)

The dynamic light scattering (DLS) measurements were carried out on 10 mmol/L peptide solutions (i.e. below the critical gelation concentration) by using a 3 DDLS spectrophotometer (LS instruments, Fribourg, Switzerland) using vertically polarized He—Ne laser light (25 mW with wavelength of 632.8 nm) with an avalanche photodiode detector at an angle of 90° at 25° C. Intensity autocorrelation functions were recorded and analyzed by means of the cumulant method in order to determine the intensity weighted diffusion coefficients D and the average hydrodynamic radius $R_h$ by using the Stokes-Einstein equation, $R_h = k_B T / 6\pi\eta D$, where $k_B$ is the Boltzmann constant, T is the absolute temperature and $\eta$ is the solvent viscosity at the given temperature.

Preparation of Tripeptide Samples

Tripeptides were dissolved in water by sonication and vortexing, followed by bringing the pH to 7.2±0.1 by dropwise addition of 0.25 M NaOH solution to a final concentration of 30 mmol/L. These were diluted to 10 mmol/L for DLS and NMR experiments. Note that the KYF gel could also be prepared by direct dissolution into a 0.1 M phosphate buffer at pH 7. Characterization of the resulting samples took places at least 24 hours after sample preparation. Samples for FTIR and NMR analysis were prepared using D2O (99.9% D) and NaOD solution instead of H2O and NaOH.

In the current work, we provide a design-oriented approach by screening all possible combinations of amino acids in tripeptides ($20^3$=8000 different sequences) and subsequently identifying those with the best predicted properties for experimental investigation.

Figure 2E:
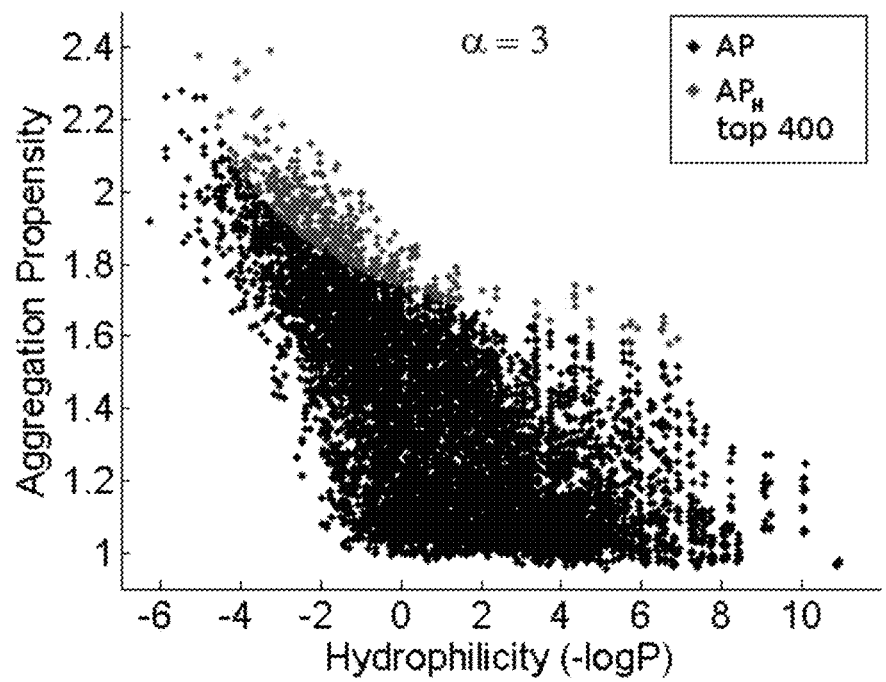

We have chosen to utilize the *MARTINI* force field, which has been extensively parameterized for amino acids (see FIG. 2(*a*)).[33-35] This force field provides a speed up compared to atomistic force fields by approximately 3 orders of magnitude, allowing access to a sufficient simulation size and length for our new screening approach. The ranking of the output of molecular simulations according to descriptors such as propensity to aggregate and hydrophilicity allows the selection of a set of candidates to form nanostructures in water.

The following description provides a simulation protocol for rapidly selecting candidates with self-assembly propensity is presented, which is subsequently adapted to favour candidates that include hydrophilic residues. The results of these simulations are analyzed in terms of aggregation propensity, structural features and general design rules and subsequently verified against the experimental results from literature. Finally, a number of new peptides with promising scores were selected from the simulation results, synthesized and analyzed with regards to their assembly behavior by diffusion ordered NMR (DOSY NMR), atomic force and transmission electron microscopy (AFM/TEM), fourier transform infrared (FTIR) spectroscopy and dynamic light scattering (DLS).

Results and Discussion

Initial Screening Phase 50 ns simulations were performed for all 8,000 tripeptides studied. From the last frame of these simulations, the Aggregation Propensity (AP, see Experimental Section) was measured. A list of high (AP>2) scoring peptides are displayed in FIGS. 3(*d*) and 3(*e*) (analogous to FIG. 3(*a*)). On average, hydrophobic tripeptides have higher AP scores and W, F, Y give rise to relatively high contribution to the AP. Remarkably, T and S also stand out as contributing strongly compared to other amino acids with similar hydrophobicity. However, a wide range of AP scores were observed with intermediately hydrophilic peptides as shown in FIG. 2(*c*), which displays the AP scores as a function of the total hydrophobicity (log P) of the tripeptide. It is noted that only a weak correlation exists between the total hydrophilicity of the tripeptide and its propensity to aggregate: while hydrophobic peptides (log P>3) always display a relatively high score and hydrophilic peptides (log P<7) have a low tendency to aggregate, intermediately hydrophilic or amphiphilic peptides exhibit a wide range of AP scores from ~1 (no aggregation) to ~2.4 (strong aggregation). This confirms that aggregation is not a process that can be predicted solely on the basis of a peptide's hydrophilicity and the simulations presented here are needed to distinguish between good and poor candidates for self-assembly.

Strongly hydrophobic peptides are often insoluble in water. However, our screening approach does not, a priori, exclude any peptide based on known practical solubility limitations. As such, hydrophobic peptides produce high AP scores. However, the simulations presented here are of insufficient size and detail to distinguish between the processes of aggregation, precipitation, crystallization or self-assembly. Therefore, in order to select a more appropriate subset of peptides for practical use we have developed a hydrophilicity-corrected score, $AP_H$, which introduces a positive bias towards hydrophilic peptides (for details see experimental methods). The inclusion of hydrophilic residues has previously been shown to transform insoluble nanofibers to a hydrogel network.[36]

FIG. 3(*a*) shows the normalized APH score for all 8000 tripeptides. The amino acids on the axes are ordered from hydrophobic to hydrophilic according to the Wimley-White scale.[37,38] It is clear that a different set of peptides is indicated as having self-assembly propensity combined with hydrophilicity when compared to FIG. 3(*d*). Contributions from peptides containing charged (K, R, D, E) and hydrogen bonding amino acids (mainly T and S) stand out more using the $AP_H$ score, which will be further discussed in the next section. The top 400 peptides selected by this protocol are indicated in FIG. 2(*c*) and Table 3 and were subjected to an extended screening phase.

Generation of Design Rules

Figure 3B:
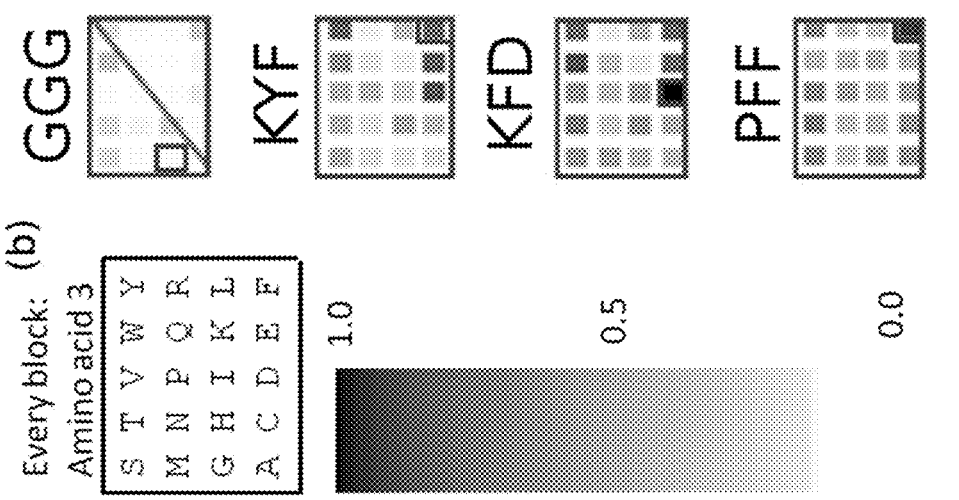
FIG. 3: shows from Screening to Design Rules. (a) Normalized $AP_H$ score for all 8000 combinations of three amino acids after a 50 ns simulation. Within every rectangle, the third amino acid is represented by the position of the coloured square at the locations indicated in the legend on the right. (b) Expansion of the highlighted areas in (a) with four peptide entries indicated. (c) Average APH scores of tripeptides with the specific amino acid on the x-axis in the N-terminal (blue), middle (red) and C-terminal position (green). A higher score indicates a higher propensity to aggregate. Amino acids are grouped by aromatic, hydrophilic, cationic and anionic side chains. (d). AP score for all 8000 combinations of three amino acids after a 50 ns simulation. Within every rectangle, the third amino acid is represented by the position of the coloured square at the locations indicated in the legend on the right.
Figure 3A:
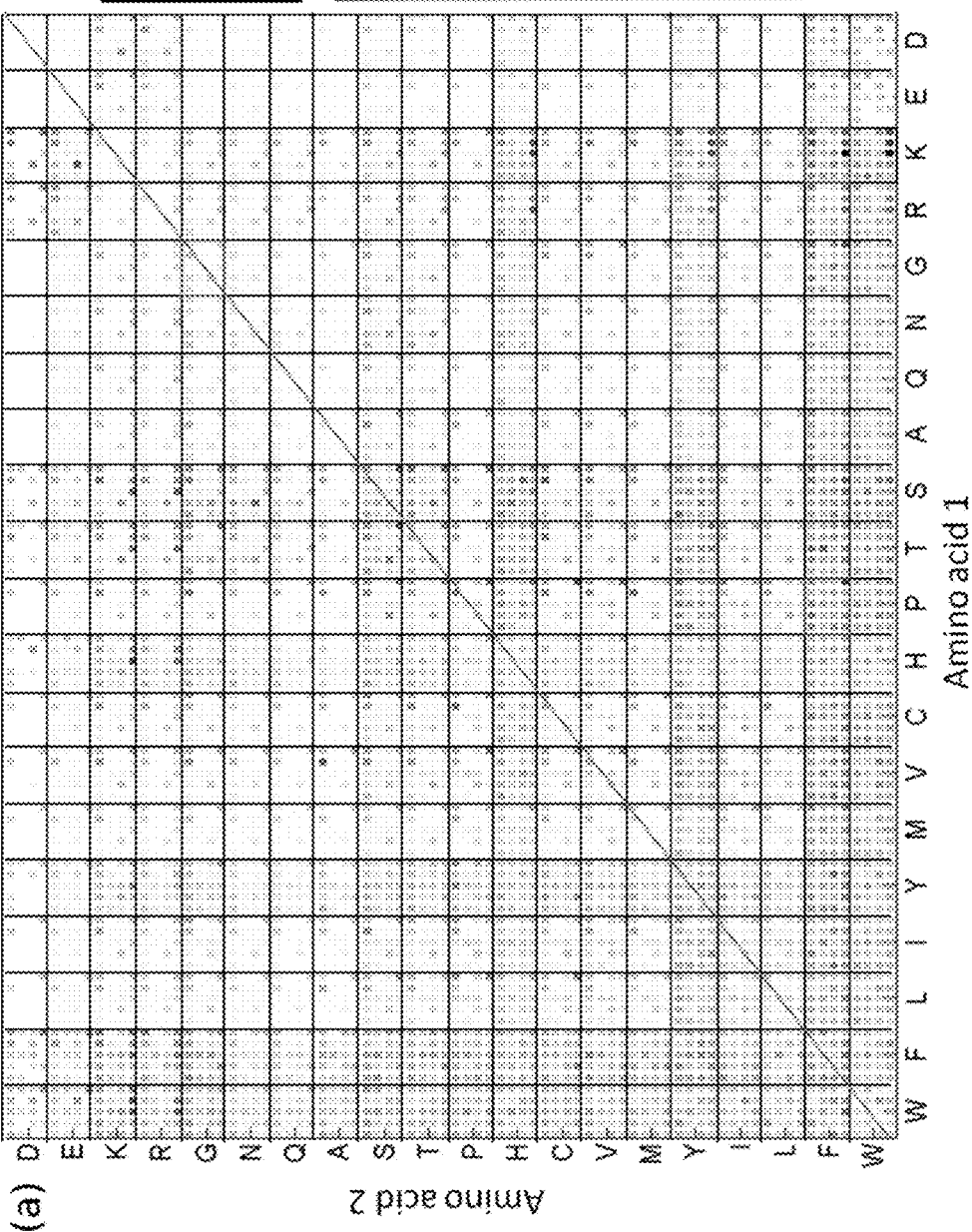
Figure 3C:
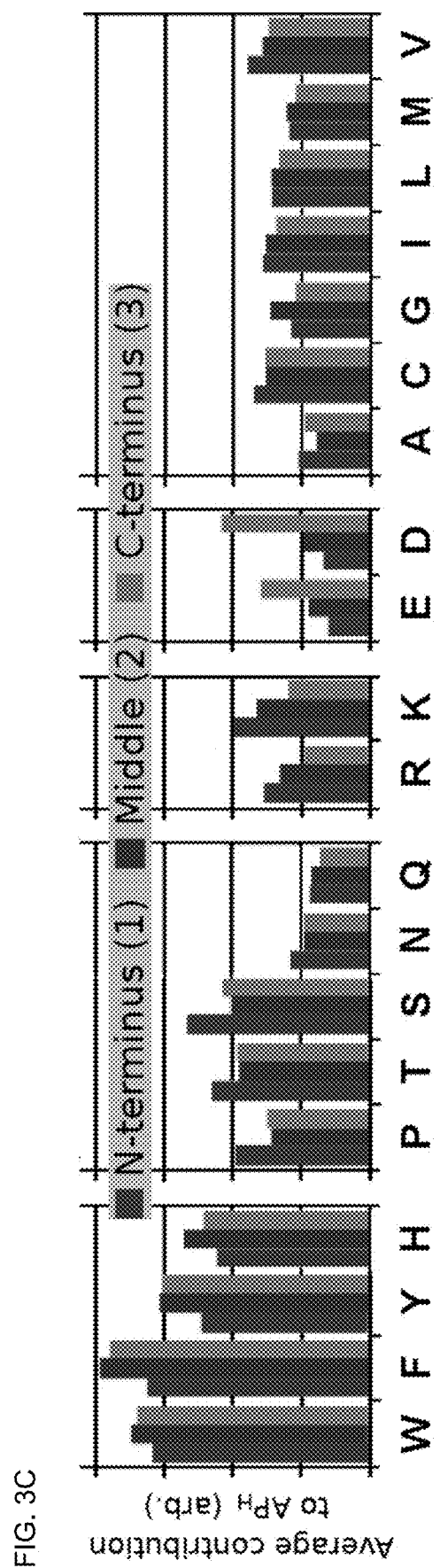
Figure 3D:
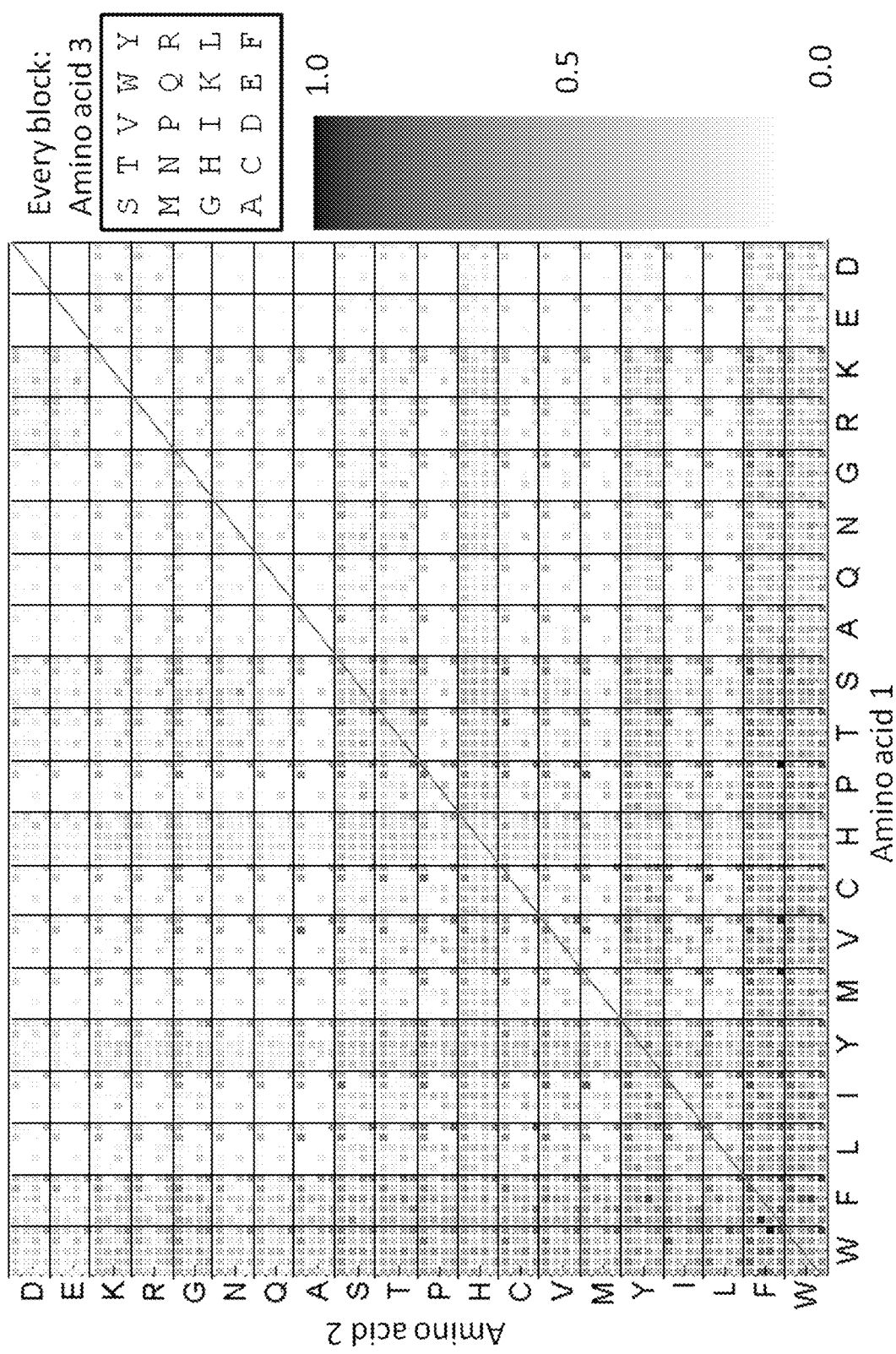

The simulation results of all 8000 tripeptides were analyzed by studying the contributions of specific amino acids to the $AP_H$ score. This allows for the determination of design rules, i.e., placement of certain amino acids in a particular position within the peptide chain to promote self-assembly. FIG. 3(c) shows the average $AP_H$ score of all peptides with a certain amino acid in position 1 (N-terminus), 2 or 3 (C-terminus). Several interesting observations were made: (I) Aromatic amino acids (F, Y and to a lesser extent W) are more favorable in position 2 and 3 compared to the N-terminal amino acid, (II) negatively charged amino acids (E and especially D) are strongly favored in position 3 and (III) positively charged and hydrogen bond donating amino acids (K, R; S, T) promote self-assembly when located at the N-terminus. Also proline is favored in position 1, which could be due to its unique conformational properties allowing better packing of the short peptides; the 'kink' in the backbone chain leading to more ordered self-assembly. These design rules were used to select a number of tripeptides from across the range of AP and $AP_H$ scores to study experimentally (see Table 1 and below).

Evaluation of Simulation Length

The emergence of structural features in peptide self-assembly takes place on timescales that are longer than the 50 ns used in the initial screening phase.[39] To test the validity of using the results of the initial 50 ns phase, the simulation time was extended to 400 ns for peptides with either a high $AP_H$ score (top 5% of 8000) or with an AP score>2 (124 peptides, 1.55%, including 53 peptides that fall in both categories), as highlighted in FIG. 2(c). This cut-off has been previously shown to be reasonable for the AP score for self-assembly candidates in the study of all dipeptides.[28] Moreover, for these simulations the standard coarse-grain water was replaced by "polarizable" coarse-grain beads, which have been shown to represent the polarizability and charge screening of water more accurately.

Table 1 shows the AP scores of the experimentally studied peptides at 50 and 400 ns. When comparing the values at 50 and 400 ns it becomes apparent that AP scores do increase slightly when extending the simulation, but no peptides were observed to change from 'not aggregating' to 'strongly aggregating' or vice versa and their relative scores remain broadly constant. Overall this data suggests that standard CG water and 50 ns simulation length is sufficient for an initial screening phase for these systems.

Evaluation of Examples from the Literature.

The top half of Table 2 shows all tripeptides that were examined for their assembling properties found in literature. CFF, FFF, LFF, VFF and FFV were reported to form extended nanostructures under mainly aqueous conditions.[8-11] All these tripeptides were found to have an AP score>2 after the 50 ns simulation, which supports that this is a reasonable cut-off for assembling peptides. Interestingly, Marchesan et al. noted that VFF (AP=2.3) showed more evidence for nanostructure formation than structural isomer FFV (AP=2.0),[10] which agrees with our observation that aromatics in the $2^{nd}$ and $3^{rd}$ position improve aggregation. KFG, reported to form vesicles and nanotubes has an AP of 1.6, but does largely obey our design rules with K at the N-terminus and F in the second position.

To study the formation of nanostructures in the simulations, the simulation time was extended even further on a larger peptide box (1200 peptides, 0.14 M in CG water) for the tripeptides studied experimentally in literature. The last frames of the MD simulations are displayed in Table 2 and are in agreement with the experimentally observed nanostructures in Table 2: FFF (experiment: spheres, plates), CFF, VYV (experiment: spheres) and FFV and LFF (experiment: fibers) match the computational result. Longer simulations on FFF were reported to produce nanospheres and nanorods, similar to the structures observed here.[31] Tripeptides DFN and ECG, which were experimentally not found to exhibit assembly in solution,[15,41] were also calculated to have a low propensity to aggregate. It should be noted that the size of the aggregates in these simulations does not compare to the experimental size of the aggregates due to the limited number of molecules in the simulation. It has become apparent the proposed computational method is mainly valuable in determining a good set of candidates for self-assembling nanostructures after 50 ns, but structural information can be obtained as well with much longer, extended, simulations as was reported previously.[28,30,31]

Model Predictive Value

The computational method outlined above was validated by comparison with experimental work from literature (vide supra). However, the added value of the proposed procedure lies in identifying new self-assembling peptides. We tested its predictive value by synthesizing and characterizing various tripeptides indicated as good candidates for nanostructure formation.

The bottom half of Table 2 contains the tripeptides that were selected for synthesis and experimental characterization. The selection was made to include a wide range of AP and $AP_H$ scores, including PFF (#1 from AP score) and KFD (#1 from $AP_H$ score) and peptides that adhere to one or more of our design rules formulated above, such as KYF. GGG is included as a non-self-assembling control peptide (AP=1.0). These peptides were dissolved in water at pH 7 and their aggregation behavior was studied in order to test the predictive value of our method. For KYF, this afforded the formation of a translucent self-supporting hydrogel, while PFF and FHF gave suspensions, IYF and FYI precipitated and the other tripeptides gave clear solutions.

To correlate the AP scores calculated with experimentally observed aggregation, the presence and size of aggregates were determined by Diffusion Ordered NMR spectroscopy (DOSY). This method is able to determine the diffusion coefficient D of supramolecular aggregates and therefore their relative size, as described by the Stokes-Einstein equation.[43,44] Diffusion constants for all the studied tripeptides can be found in Table 2. FIG. 4(d) displays the α-proton region of the DOSY spectra of KYF, KFD and GGG. The poor solubility of PFF, FHF, IYF and FYI prevented reliable extraction of aggregate size for these peptides. For the remaining peptides, DOSY results are in good agreement with the predicted aggregation propensity at 50 ns. As expected, the negative control GGG has the highest diffusion constant. KFD has a relatively low AP and shows an intermediate diffusion rate. KYF has the lowest diffusion constant, consistent with its tendency to form an aggregated hydrogel structure. It can be seen from FIG. 2(c) and Table 2 that KYF ranks high on the $AP_H$ score (#28 out of 8000), again demonstrating the value of taking the hydrophilicity of peptides into account (KYF only ranks #478 in the AP score). Note that peptide RYF (#212, $AP_H$ score) did not give a gel and SYF (#380, $AP_H$ score) was insoluble in water (data not shown).

Further studies were employed to elucidate the nanostructural components of KYF (gel), KFD (#1 from $AP_H$ score), PFF (#1 from AP score) and GGG (negative control) specifically, using FTIR spectroscopy, DLS and TEM.

The secondary structure of the peptides can be probed by infrared (IR) spectroscopy.[45,46] When aggregation takes place via intermolecular hydrogen bonding of the amide groups, the 1650-1655 cm$^{-1}$ absorption observed for free peptides in solution typically narrows and shifts to lower frequency, while the 1595 cm$^{-1}$ peak, assigned to carboxylate groups, broadens or decreases in intensity due to protonation or salt bridge formation. This was clearly observed for PFF in FIG. 3(e), as the amide I absorption shifts to 1637 cm$^{-1}$ and significantly narrows compared to non-aggregating peptide GGG, consistent with a β-sheet like arrangement of the amide groups. KFD shows no significant narrowing of the amide absorption compared to GGG, indicating no extended secondary structure formation. Note that small absorption maxima in the 1670-1685 cm$^{-1}$ region are assigned to residual trifluoro-acetic acid absorption and the 1570-1580 cm$^{-1}$ band for KFD is assigned to the aspartic acid side chain carboxylate group.

For KYF, a dramatic change in the amide region was noticed upon gelation with intense IR absorption peaks at 1621 and 1649 cm$^{-1}$ for the amide groups and 1568 cm$^{-1}$ for salt-bridged carboxylate groups. This indicates strong intramolecular hydrogen bonding between amide modes and strong interactions of the N-terminus or lysine side chains with the C-terminus, both suggesting a well-ordered peptide nanostructure.[45,46]

To further confirm the presence (and size) of the peptide aggregates formed, dynamic light scattering (DLS) experiments were performed on the KYF gel, PFF suspension and KFD and GGG solutions. FIG. 3(h) shows the intensity auto-correlation function and the average hydrodynamic radius of the aggregates determined from the extracted diffusion constant. The relative size of the aggregates (0.26, 0.13, 0.70 and 0.10 μm for KYF, KFD, PFF and GGG, respectively) is in reasonable agreement with the relative AP scores for these peptides as predicted by the MD simulations (Table 2), although it was surprising to see such large aggregates for GGG.

Figures 4A, 4B, 4C:
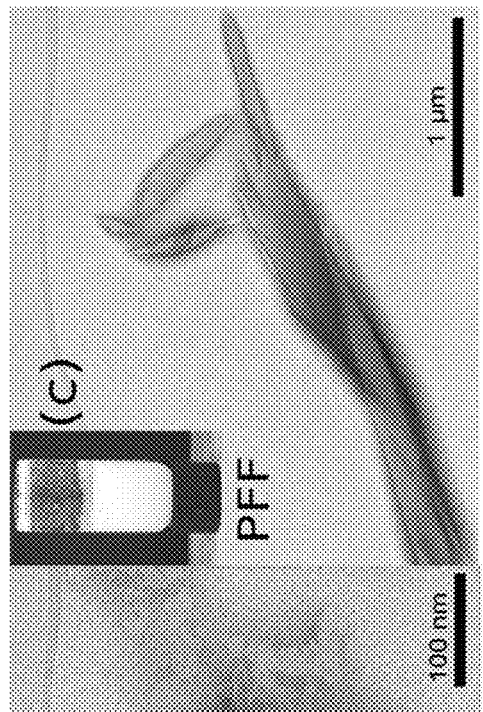
FIG. 4 shows the Characterization of Selected Tripeptides. (a-c) TEM images of KYF, KFD and PFF tripeptides. Insets show photos of the gel, solution and suspension, respectively. (d) α-proton region of the DOSY spectra for KYF, KFD and GGG tripeptides at 10 mM at pH 7. Horizontal lines indicate the value for the logarithm of the diffusion constant D. Note that PFF is not included due to its low solubility. (e) FTIR absorption spectra in the amide I region of tripeptides (30 mM in D2O at pH 7): KYF, PFF (and KFD and GGG. Spectra have been vertically offset for clarity. (f) DLS auto-correlation functions for KYF, KFD, PFF and GGG (10 mM at pH 7). The inset shows the hydrodynamic radii (RH in nm) and AP scores at 50 ns for the four peptides.
Figure 4D:
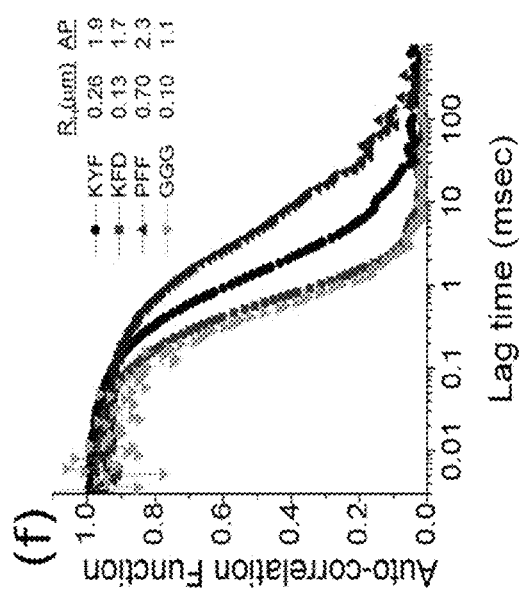
Figure 4E:
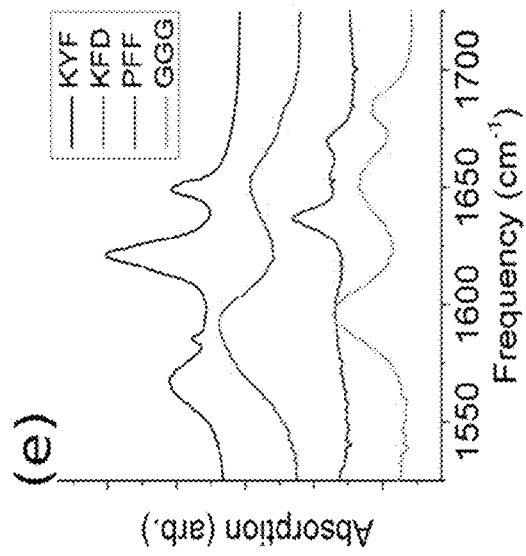
Figure 4F:
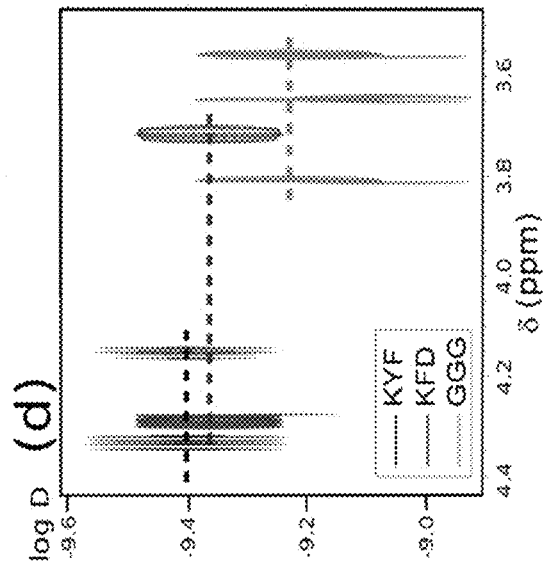

For the peptides synthesized here, TEM studies on KYF, PFF and KFD reveal an entangled fibrous network for the KYF hydrogel (FIG. 4(a)). Although KYF was not observed to form fibers after 1200 ns in the MD simulation, further extension of the simulation to 4800 ns resulted in a branched fibrous nanostructure spanning the whole simulation box. TEM images of PFF (FIG. 4(b)) reveal short crystalline nanostructures with a large aspect ratio, while KFD (FIG. 4(c)) was observed to form strongly curved fibers together with more amorphous regions.

Investigation into the pH Dependence on the Gelation Behaviour of the KYF Hydrogelator We investigated the effects of pH on the gelation of the tripeptide KYF in aqueous solvent. Infrared spectroscopy of the KYF gel shows that the formation of a salt bridge plays a significant role in the self-assembly of KYF. The alteration of the pH will affect the protonation state of the ionisable groups on KYF i.e., N and C termini and the lysine side groups. Herein, the inventors demonstrate that by changing the pH of an aqueous solution of KYF, gelation can be induced.

pH measurements were carried out ranging from pH 5 to 8. At each pH measurement an image was taken to show the gelation behaviour. The pH was altered using 0.5M NaOH which is added drop wise into the vial, vortexed to ensure a complete mix then the pH is measured until a stable value is obtained.

Initially, the peptide sample is dissolve in water and the pH is recorded. At this point the pH is below the pKa of the C-terminus therefore the terminal acid is protonated and gelation should not occur, which is what was observed.

On changing the pH of the sample from 2.21 to 6.7 similar results were obtained.

Namely, these samples remained as a clear solution and the gel state was not observed. However, as the pH is increased to 6.9 a weak gel is formed. A tilted vial showed the presence of a gel material but on moving the vial the gel collapsed and water began to separate out. At pH 7.05 a stronger gel is formed. At this point the vial can be rotated fully showing a self-supporting hydrogel. On increasing the pH from 7.05 until 7.98, we observed the formation of stronger gels. Moreover, it was noted that there is an increase in turbidity of the gel, i.e., on increasing the pH the gel become cloudier.

CONCLUSIONS

We have presented a coarse-grain MD protocol for screening peptides for their aggregation behavior and applied this to the set of 8000 gene-encoded tripeptides. After an initial 50 ns screening phase a subset of peptides was selected based on their aggregation propensity (AP) and hydrophilicity-corrected AP (AP$_H$). This set was then used in extended simulations to study the tripeptide dynamics and nanostructure formation.

The simulation results indicate only a weak correlation between hydrophilicity and AP, confirming that self-assembly propensity is not simply a measure of hydrophobicity and clearly illustrating the usefulness of MD simulations for selection of self-assembling peptides. Furthermore, a set of design rules that promote aggregation was described, where aromatic amino acids are most favorable in positions 2 and 3 in a tripeptide, while positive and H-bonding residues favor position 1 (N-terminus) and negative residues position 3 (C-terminus).

The results of the simulations were validated by comparison with experimental results from literature and by synthesis and characterization of a set of tripeptides which are indicated by our method and design rules to be promising candidates for self-assembly. Interestingly, this led to the discovery of the first unprotected full-L tripeptide (KYF) that forms a hydrogel in the absence of organic solvents. More generally, excellent agreement was observed between predicted AP scores and experimental behavior. These results support further exploitation of the protocol for screening larger peptides in the search for new nanostructures.

Finally, in this current work we have presented a selection method based on the hydrophilicity of the tripeptides. However, it is clear that depending on the desired properties of the self-assembling peptide filters can be added, such as automated screening based on the shape of nanostructure,[47] peptide foldability,[48] the presence of certain amino acid interactions or other molecular properties, such as protonation state of the amino acids alone and/or when part of a peptide sequence could be equally useful and constitute further additions.

In the pH experiments, it is noted that the critical gelation occurs at a pH that is very close to neutral (6.9-7.05). This result was unexpected based on the pKa values of the ionisable groups (C-terminal, N-terminal, and lysine side-chain) in the peptide. Clearly, the hydrophobic environment that is created upon assembly of the KYF peptide causes a tunable shift in pKa (tunable by hydrophobicity of the overall peptide) of one or more of its ionisable moieties.

The pH dependence on the gelation of KYF has been demonstrated. We have seen that at neutral pH ranges hydrogelation occurs, but at lower pH ranges no gelation is observed. There is clearly a relationship between the ability of the tripeptide to form a nanofibrous network that is capable of forming a gel and the protonation states of the amino acids that compose the tripeptide. This principle could be more generally extended to other tripeptides that we have shown to form hydrogels, or that could be designed to form hydrogels following the rules described herein. In particular, those peptides that score high on the $AP_H$ score are candidates for pH dependent self-assembly.

Finally, the screening approach that is described herein can be adopted to screen for the ability of the tripeptides to self-assemble within various protonation states by altering the bead types that describe the amino acids within the coarse grained model. The beads that describe the groups of atoms within the amino acid are parameterised to represent the vdW parameters and charge states of the atoms that comprise the bead. Therefore, by changing the bead from a positive (negative) to neutral bead type, or vice versa, with the associated change in the vdW parameters, allows us to model the different protonation states of the amino acids that compose the tripeptide. This approach would add an additional filter to the screening process described herein, whereby the aggregation propensity (AP), the hydrophilicity and the protonation states of the amino acids would all be analysed to determine whether a tripeptide will be able to form a pH dependent gel state.

TABLE 1

AP scores after 50, 400 and 1200 ns.

| Trip. | AP 50 ns[a] | AP 50 ns[b] | AP 400 ns[b] | AP 1200 ns[c] |
|---|---|---|---|---|
| CFF | 2.05 | 2.21 | 3.04 | 3.70 |
| DFN | 1.17 | 1.10 | 1.11 | 1.28 |
| ECG | 1.01 | 1.02 | 0.99 | 1.05 |
| FFF | 2.26 | 2.44 | 2.42 | 3.44 |
| FFV | 2.03 | 2.21 | 2.84 | 3.91 |
| KFG | 1.56 | 1.39 | 1.57 | 1.94 |
| LFF | 2.07 | 2.41 | 2.70 | 3.34 |
| VFF | 2.33 | 2.24 | 2.92 | 3.82 |
| VYV | 1.88 | 1.78 | 2.44 | 2.67 |
| PFF | 2.39 | 2.20 | 3.51 | 3.70 |
| FYI | 2.22 | 2.12 | 2.24 | 3.19 |
| FHF | 2.09 | 1.95 | 3.22 | 3.17 |
| YFI | 1.97 | 1.93 | 2.15 | 3.11 |
| IYF | 1.89 | 2.26 | 2.18 | 3.24 |
| KYF | 1.85 | 1.70 | 1.83 | 3.19 |
| KFD | 1.73 | 1.40 | 1.70 | 2.33 |
| KHD | 1.63 | 1.44 | 1.92 | 2.51 |
| KFF | 1.92 | 1.72 | 2.01 | 2.66 |
| KYY | 1.79 | 1.58 | 1.88 | 3.03 |
| KYW | 1.78 | 1.76 | 1.99 | 2.87 |
| KLL | 1.31 | 1.06 | 1.08 | 1.38 |
| FYK | 1.73 | 1.63 | 1.67 | 2.59 |
| RYF | 1.80 | 1.60 | 1.98 | 2.66 |
| GGG | 1.07 | 1.07 | 1.04 | 1.11 |

[a]300 peptides in standard CG water, 0.23M,
[b]300 peptides in polarizable CG water, 0.23M,
[c]1200 peptides in standard CG water, 0.14M

TABLE 3

Table S5: peptides from the top 400 $AP_H$

| pep | AP | logP | AP_H |
|---|---|---|---|
| KFD | 1.73 | 4.73 | 0.187 |
| KWD | 1.74 | 4.35 | 0.186 |
| HKD | 1.65 | 6.55 | 0.176 |
| PFF | 2.39 | -3.28 | 0.174 |
| KWE | 1.72 | 4.34 | 0.174 |
| WKE | 1.71 | 4.34 | 0.169 |
| KHD | 1.63 | 6.55 | 0.167 |
| PCF | 2.08 | -1.59 | 0.167 |
| KWF | 2.00 | -1.00 | 0.163 |
| KFW | 2.00 | -1.00 | 0.163 |
| KHE | 1.62 | 6.54 | 0.161 |
| TSF | 1.99 | -1.00 | 0.161 |
| SCW | 2.06 | -1.65 | 0.161 |
| WKD | 1.69 | 4.35 | 0.160 |
| KYD | 1.64 | 5.73 | 0.160 |
| KEH | 1.62 | 6.54 | 0.159 |
| GFF | 2.14 | -2.27 | 0.158 |
| VAW | 2.10 | -2.05 | 0.158 |
| SSF | 1.96 | -0.79 | 0.155 |
| KYE | 1.63 | 5.72 | 0.155 |
| STF | 1.97 | -1.00 | 0.154 |
| SRD | 1.62 | 5.91 | 0.154 |
| KYY | 1.79 | 1.38 | 0.152 |
| PVF | 2.08 | -2.03 | 0.152 |
| SKD | 1.59 | 6.90 | 0.152 |
| TFP | 2.00 | -1.32 | 0.152 |
| RHD | 1.63 | 5.56 | 0.151 |
| KYF | 1.85 | 0.38 | 0.151 |
| FKF | 1.92 | -0.62 | 0.150 |
| KFF | 1.92 | -0.62 | 0.150 |
| WFD | 1.88 | -0.16 | 0.149 |
| WRD | 1.69 | 3.36 | 0.149 |
| FKD | 1.65 | 4.73 | 0.148 |
| PHF | 2.00 | -1.46 | 0.148 |
| KFY | 1.84 | 0.38 | 0.147 |
| KFE | 1.64 | 4.72 | 0.147 |
| PPF | 1.99 | -1.43 | 0.147 |
| SFE | 1.73 | 2.38 | 0.147 |
| SNH | 1.78 | 1.42 | 0.147 |
| WKF | 1.94 | -1.00 | 0.146 |
| CPW | 2.05 | -1.97 | 0.145 |
| SYS | 1.84 | 0.21 | 0.145 |
| VPF | 2.05 | -2.03 | 0.144 |
| PYY | 1.96 | -1.28 | 0.143 |
| YFK | 1.83 | 0.38 | 0.143 |
| TKD | 1.58 | 6.69 | 0.143 |
| FKY | 1.82 | 0.38 | 0.142 |
| KDF | 1.63 | 4.73 | 0.141 |
| LCF | 2.18 | -2.98 | 0.140 |
| TCW | 2.01 | -1.86 | 0.140 |
| GFY | 1.95 | -1.27 | 0.140 |
| TGF | 1.87 | -0.31 | 0.140 |
| SWE | 1.73 | 2.00 | 0.139 |
| STY | 1.84 | 0.00 | 0.139 |
| TYF | 2.05 | -2.17 | 0.139 |
| PMW | 2.11 | -2.62 | 0.139 |
| PSF | 1.93 | -1.11 | 0.139 |
| TFV | 2.02 | -1.92 | 0.138 |
| SKW | 1.77 | 1.17 | 0.138 |
| SFD | 1.71 | 2.39 | 0.138 |
| SPF | 1.93 | -1.11 | 0.138 |
| PGW | 1.90 | -0.80 | 0.137 |
| FFD | 1.82 | 0.22 | 0.137 |
| KFT | 1.75 | 1.34 | 0.136 |
| PPW | 1.99 | -1.81 | 0.136 |
| RWD | 1.66 | 3.36 | 0.136 |
| TRD | 1.59 | 5.70 | 0.136 |
| PFT | 1.94 | -1.32 | 0.135 |
| FCC | 1.98 | -1.75 | 0.135 |
| RFY | 1.87 | -0.61 | 0.135 |
| PIY | 1.97 | -1.69 | 0.134 |
| RFD | 1.64 | 3.74 | 0.134 |
| SHK | 1.66 | 3.37 | 0.134 |
| SHN | 1.74 | 1.42 | 0.133 |
| YKD | 1.58 | 5.73 | 0.133 |
| SGF | 1.83 | -0.10 | 0.133 |
| HRD | 1.58 | 5.56 | 0.132 |
| VVF | 2.08 | -2.63 | 0.131 |
| TSH | 1.76 | 0.82 | 0.131 |
| FRY | 1.86 | -0.61 | 0.130 |
| TTF | 1.91 | -1.21 | 0.130 |

TABLE 3-continued

Table S5: peptides from the top 400 AP$_H$

| pep | AP | logP | AP_H |
|---|---|---|---|
| FKW | 1.89 | −1.00 | 0.130 |
| YPV | 1.89 | −1.03 | 0.129 |
| PTF | 1.91 | −1.32 | 0.128 |
| VFF | 2.33 | −3.88 | 0.128 |
| CFV | 2.01 | −2.19 | 0.128 |
| SFY | 1.98 | −1.96 | 0.128 |
| PCW | 1.98 | −1.97 | 0.128 |
| CSY | 1.82 | −0.27 | 0.128 |
| YFC | 2.04 | −2.44 | 0.128 |
| SWP | 1.93 | −1.49 | 0.128 |
| FVV | 2.07 | −2.63 | 0.127 |
| SGW | 1.84 | −0.48 | 0.127 |
| ISW | 2.08 | −2.75 | 0.127 |
| CFC | 1.95 | −1.75 | 0.126 |
| IFG | 1.94 | −1.68 | 0.126 |
| KVW | 1.78 | 0.25 | 0.126 |
| YFD | 1.73 | 1.22 | 0.126 |
| FDF | 1.78 | 0.22 | 0.126 |
| SYH | 1.81 | −0.14 | 0.126 |
| SHF | 1.88 | −1.14 | 0.125 |
| VFG | 1.87 | −1.02 | 0.125 |
| WRE | 1.63 | 3.35 | 0.125 |
| KDW | 1.60 | 4.35 | 0.125 |
| PYV | 1.87 | −1.03 | 0.125 |
| TYT | 1.81 | −0.21 | 0.124 |
| FYI | 2.22 | −3.54 | 0.124 |
| PFY | 2.00 | −2.28 | 0.124 |
| YPY | 1.89 | −1.28 | 0.124 |
| VFD | 1.71 | 1.47 | 0.124 |
| PFV | 1.97 | −2.03 | 0.124 |
| SFW | 2.18 | −3.34 | 0.124 |
| WFG | 2.05 | −2.65 | 0.124 |
| TFC | 1.91 | −1.48 | 0.123 |
| PFS | 1.87 | −1.11 | 0.123 |
| STH | 1.74 | 0.82 | 0.123 |
| FGS | 1.79 | −0.10 | 0.123 |
| VYY | 1.95 | −1.88 | 0.123 |
| FRD | 1.61 | 3.74 | 0.123 |
| VSW | 1.97 | −2.09 | 0.122 |
| VFE | 1.70 | 1.46 | 0.122 |
| KDY | 1.55 | 5.73 | 0.122 |
| CMF | 2.01 | −2.40 | 0.122 |
| PSY | 1.79 | −0.11 | 0.122 |
| YGF | 1.88 | −1.27 | 0.122 |
| MFY | 2.12 | −3.09 | 0.122 |
| MFF | 2.36 | −4.09 | 0.122 |
| TFD | 1.67 | 2.18 | 0.121 |
| SHD | 1.59 | 4.21 | 0.121 |
| SWK | 1.71 | 1.17 | 0.121 |
| RDF | 1.61 | 3.74 | 0.121 |
| IFT | 2.03 | −2.58 | 0.121 |
| LPF | 2.07 | −2.82 | 0.121 |
| VCF | 1.98 | −2.19 | 0.121 |
| LFD | 1.74 | 0.68 | 0.120 |
| KPF | 1.71 | 1.23 | 0.120 |
| TYD | 1.63 | 3.18 | 0.120 |
| RYD | 1.58 | 4.74 | 0.120 |
| TKF | 1.70 | 1.34 | 0.120 |
| SVW | 1.96 | −2.09 | 0.120 |
| TWC | 1.94 | −1.86 | 0.120 |
| CTW | 1.94 | −1.86 | 0.120 |
| KWM | 1.77 | 0.04 | 0.120 |
| GFW | 2.04 | −2.65 | 0.120 |
| GFT | 1.80 | −0.31 | 0.120 |
| KYW | 1.78 | 0.00 | 0.120 |
| VAF | 1.91 | −1.67 | 0.119 |
| HRE | 1.55 | 5.55 | 0.119 |
| IYY | 2.02 | −2.54 | 0.119 |
| PSW | 1.89 | −1.49 | 0.119 |
| VWK | 1.76 | 0.25 | 0.119 |
| SGY | 1.72 | 0.90 | 0.119 |
| HKE | 1.53 | 6.54 | 0.118 |
| AFY | 1.94 | −1.92 | 0.118 |
| SYY | 1.84 | −0.96 | 0.118 |
| RWE | 1.61 | 3.35 | 0.118 |
| CYH | 1.82 | −0.62 | 0.118 |
| SCY | 1.79 | −0.27 | 0.118 |
| CFG | 1.81 | −0.58 | 0.118 |
| KEW | 1.58 | 4.34 | 0.118 |
| KWC | 1.73 | 0.69 | 0.118 |
| VFP | 1.95 | −2.03 | 0.118 |
| SHS | 1.71 | 1.03 | 0.118 |
| SWH | 1.89 | −1.52 | 0.118 |
| PLY | 1.92 | −1.82 | 0.117 |
| SKE | 1.52 | 6.89 | 0.117 |
| TFT | 1.86 | −1.21 | 0.117 |
| HKF | 1.70 | 1.20 | 0.117 |
| FTC | 1.88 | −1.48 | 0.117 |
| TYI | 1.89 | −1.58 | 0.117 |
| CLW | 2.15 | −3.36 | 0.117 |
| FIS | 1.98 | −2.37 | 0.116 |
| PWH | 1.92 | −1.84 | 0.116 |
| VFK | 1.73 | 0.63 | 0.116 |
| KLF | 1.77 | −0.16 | 0.116 |
| CFD | 1.66 | 1.91 | 0.116 |
| PWF | 2.21 | −3.66 | 0.116 |
| PVW | 1.99 | −2.41 | 0.116 |
| CYF | 1.99 | −2.44 | 0.116 |
| PCY | 1.80 | −0.59 | 0.116 |
| VFC | 1.96 | −2.19 | 0.116 |
| TSY | 1.76 | 0.00 | 0.116 |
| WDF | 1.77 | −0.16 | 0.116 |
| FMC | 1.98 | −2.40 | 0.116 |
| LPY | 1.91 | −1.82 | 0.115 |
| FKE | 1.56 | 4.72 | 0.115 |
| YFG | 1.86 | −1.27 | 0.115 |
| THS | 1.71 | 0.82 | 0.115 |
| WEF | 1.77 | −0.17 | 0.115 |
| YCC | 1.81 | −0.75 | 0.115 |
| WSY | 1.97 | −2.34 | 0.115 |
| LSF | 1.99 | −2.50 | 0.115 |
| KDH | 1.52 | 6.55 | 0.115 |
| IYC | 1.91 | −1.85 | 0.115 |
| FSM | 1.92 | −1.92 | 0.115 |
| CPF | 1.89 | −1.59 | 0.115 |
| SWT | 1.87 | −1.38 | 0.115 |
| KMW | 1.76 | 0.04 | 0.115 |
| ASW | 1.84 | −1.13 | 0.115 |
| FYT | 1.95 | −2.17 | 0.115 |
| KIW | 1.79 | −0.41 | 0.115 |
| THF | 1.86 | −1.35 | 0.114 |
| PKW | 1.71 | 0.85 | 0.114 |
| MHF | 1.96 | −2.27 | 0.114 |
| VWH | 1.98 | −2.44 | 0.114 |
| VGW | 1.86 | −1.40 | 0.114 |
| FYK | 1.73 | 0.38 | 0.114 |
| CWP | 1.92 | −1.97 | 0.114 |
| KTF | 1.68 | 1.34 | 0.114 |
| EFW | 1.77 | −0.17 | 0.114 |
| FFM | 2.31 | −4.09 | 0.114 |
| RYF | 1.80 | −0.61 | 0.114 |
| GFI | 1.89 | −1.68 | 0.114 |
| FRE | 1.59 | 3.73 | 0.114 |
| PWV | 1.97 | −2.41 | 0.114 |
| CGY | 1.73 | 0.42 | 0.113 |
| PFA | 1.83 | −1.07 | 0.113 |
| SWC | 1.89 | −1.65 | 0.113 |
| PFC | 1.88 | −1.59 | 0.113 |
| KFH | 1.69 | 1.20 | 0.113 |
| VFS | 1.89 | −1.71 | 0.113 |
| CFY | 1.98 | −2.44 | 0.113 |
| VYV | 1.88 | −1.63 | 0.113 |
| PTY | 1.77 | −0.32 | 0.113 |
| IFP | 2.01 | −2.69 | 0.113 |
| SHT | 1.71 | 0.82 | 0.113 |
| PSH | 1.71 | 0.71 | 0.113 |
| SCF | 1.85 | −1.27 | 0.113 |
| KFV | 1.71 | 0.63 | 0.112 |
| REY | 1.56 | 4.73 | 0.112 |
| PHS | 1.71 | 0.71 | 0.112 |
| FFR | 1.88 | −1.61 | 0.112 |
| VYF | 2.04 | −2.88 | 0.112 |

TABLE 3-continued

Table S5: peptides from the top 400 AP$_H$

| pep | AP | logP | AP_H |
|---|---|---|---|
| FFE | 1.74 | 0.21 | 0.112 |
| FSP | 1.83 | −1.11 | 0.112 |
| KWT | 1.69 | 0.96 | 0.112 |
| CWM | 2.02 | −2.78 | 0.112 |
| WPP | 1.90 | −1.81 | 0.112 |
| YKF | 1.73 | 0.38 | 0.112 |
| TSW | 1.85 | −1.38 | 0.112 |
| RHE | 1.53 | 5.55 | 0.111 |
| GFL | 1.89 | −1.81 | 0.111 |
| KEY | 1.53 | 5.72 | 0.111 |
| FGF | 1.95 | −2.27 | 0.111 |
| FVS | 1.88 | −1.71 | 0.111 |
| CTF | 1.86 | −1.48 | 0.111 |
| WWK | 1.85 | −1.38 | 0.111 |
| KIF | 1.75 | −0.03 | 0.111 |
| WFK | 1.82 | −1.00 | 0.111 |
| KWL | 1.78 | −0.54 | 0.111 |
| FWE | 1.76 | −0.17 | 0.111 |
| RFF | 1.87 | −1.61 | 0.111 |
| SFG | 1.75 | −0.10 | 0.111 |
| SFC | 1.84 | −1.27 | 0.111 |
| PHV | 1.76 | −0.21 | 0.111 |
| STS | 1.68 | 1.17 | 0.111 |
| KHW | 1.70 | 0.82 | 0.111 |
| IGY | 1.79 | −0.68 | 0.111 |
| VFH | 1.92 | −2.06 | 0.111 |
| KSF | 1.66 | 1.55 | 0.110 |
| CYS | 1.76 | −0.27 | 0.110 |
| SKH | 1.59 | 3.37 | 0.110 |
| FYP | 1.94 | −2.28 | 0.110 |
| YWD | 1.70 | 0.84 | 0.110 |
| TGS | 1.65 | 1.86 | 0.110 |
| VKW | 1.73 | 0.25 | 0.110 |
| TWD | 1.65 | 1.80 | 0.110 |
| FYD | 1.68 | 1.22 | 0.110 |
| KFS | 1.66 | 1.55 | 0.110 |
| RDW | 1.59 | 3.36 | 0.110 |
| SSY | 1.73 | 0.21 | 0.110 |
| PYT | 1.76 | −0.32 | 0.110 |
| WYT | 1.98 | −2.55 | 0.110 |
| PAW | 1.85 | −1.45 | 0.109 |
| FYC | 1.96 | −2.44 | 0.109 |
| WGT | 1.79 | −0.69 | 0.109 |
| VTW | 1.94 | −2.30 | 0.109 |
| FGC | 1.78 | −0.58 | 0.109 |
| SFF | 2.04 | −2.96 | 0.109 |
| KSW | 1.67 | 1.17 | 0.109 |
| YFM | 2.06 | −3.09 | 0.109 |
| WST | 1.84 | −1.38 | 0.109 |
| IPY | 1.87 | −1.69 | 0.109 |
| TWY | 1.97 | −2.55 | 0.109 |
| YYI | 1.97 | −2.54 | 0.109 |
| PWT | 1.87 | −1.70 | 0.109 |
| WHP | 1.89 | −1.84 | 0.109 |
| VKF | 1.70 | 0.63 | 0.109 |
| PFG | 1.76 | −0.42 | 0.109 |
| SVY | 1.78 | −0.71 | 0.108 |
| TFF | 2.07 | −3.17 | 0.108 |
| FLP | 2.01 | −2.82 | 0.108 |
| CYC | 1.79 | −0.75 | 0.108 |
| CGF | 1.77 | −0.58 | 0.108 |
| RWY | 1.81 | −0.99 | 0.108 |
| PWC | 1.90 | −1.97 | 0.108 |
| PPY | 1.76 | −0.43 | 0.108 |
| PYS | 1.74 | −0.11 | 0.108 |
| SWN | 1.79 | −0.78 | 0.108 |
| WEK | 1.55 | 4.34 | 0.108 |
| FHF | 2.09 | −3.31 | 0.108 |
| KEF | 1.54 | 4.72 | 0.108 |
| CKW | 1.69 | 0.69 | 0.108 |
| RFE | 1.57 | 3.73 | 0.108 |
| KHF | 1.67 | 1.20 | 0.108 |
| SYT | 1.73 | 0.00 | 0.107 |
| TSS | 1.67 | 1.17 | 0.107 |
| FWD | 1.74 | −0.16 | 0.107 |
| TKH | 1.59 | 3.16 | 0.107 |
| FRF | 1.86 | −1.61 | 0.107 |
| SRE | 1.51 | 5.90 | 0.107 |
| SHP | 1.69 | 0.71 | 0.107 |
| SGS | 1.63 | 2.07 | 0.107 |
| SFH | 1.81 | −1.14 | 0.107 |
| WKY | 1.73 | 0.00 | 0.107 |
| FFA | 2.02 | −2.92 | 0.107 |
| WFE | 1.74 | −0.17 | 0.107 |
| WFT | 2.13 | −3.55 | 0.107 |
| YFE | 1.66 | 1.21 | 0.106 |
| GVF | 1.80 | −1.02 | 0.106 |
| CCY | 1.78 | −0.75 | 0.106 |
| TFL | 1.98 | −2.71 | 0.106 |
| SGH | 1.64 | 1.72 | 0.106 |
| RYE | 1.54 | 4.73 | 0.106 |
| IFA | 1.93 | −2.33 | 0.106 |
| FGV | 1.80 | −1.02 | 0.106 |
| FKS | 1.65 | 1.55 | 0.106 |
| VWV | 2.03 | −3.01 | 0.106 |
| CYW | 2.00 | −2.82 | 0.106 |
| YFS | 1.89 | −1.96 | 0.106 |
| FSV | 1.86 | −1.71 | 0.106 |
| TDW | 1.63 | 1.80 | 0.105 |
| SIY | 1.83 | −1.37 | 0.105 |
| KWW | 1.83 | −1.38 | 0.105 |
| FFG | 1.92 | −2.27 | 0.105 |
| KIY | 1.67 | 0.97 | 0.105 |
| FWP | 2.15 | −3.66 | 0.105 |
| CSF | 1.82 | −1.27 | 0.105 |
| EKW | 1.55 | 4.34 | 0.105 |
| CWD | 1.64 | 1.53 | 0.105 |
| FSL | 1.95 | −2.50 | 0.105 |
| FTP | 1.82 | −1.32 | 0.105 |
| FFC | 2.10 | −3.44 | 0.105 |
| TWG | 1.77 | −0.69 | 0.105 |
| FTL | 1.97 | −2.71 | 0.105 |
| TKY | 1.61 | 2.34 | 0.104 |
| PWI | 2.03 | −3.07 | 0.104 |
| SRW | 1.71 | 0.18 | 0.104 |
| KFI | 1.72 | −0.03 | 0.104 |
| WLT | 2.03 | −3.09 | 0.104 |
| SMY | 1.78 | −0.92 | 0.104 |
| HDK | 1.49 | 6.55 | 0.104 |
| THT | 1.69 | 0.61 | 0.104 |
| KSD | 1.48 | 6.90 | 0.104 |
| WKT | 1.67 | 0.96 | 0.104 |
| FYG | 1.81 | −1.27 | 0.104 |
| GCW | 1.79 | −0.96 | 0.104 |
| SRF | 1.69 | 0.56 | 0.104 |
| MFD | 1.65 | 1.26 | 0.104 |
| IKW | 1.75 | −0.41 | 0.104 |
| WSS | 1.80 | −1.17 | 0.104 |
| VHS | 1.71 | 0.11 | 0.104 |
| TTH | 1.68 | 0.61 | 0.104 |
| SYP | 1.73 | −0.11 | 0.104 |
| WKS | 1.66 | 1.17 | 0.104 |
| FGI | 1.85 | −1.68 | 0.104 |
| VMW | 2.05 | −3.22 | 0.103 |
| TKW | 1.67 | 0.96 | 0.103 |
| SWA | 1.80 | −1.13 | 0.103 |
| SYK | 1.60 | 2.55 | 0.103 |
| FFT | 2.04 | −3.17 | 0.103 |
| SNY | 1.68 | 0.60 | 0.103 |
| SNF | 1.74 | −0.40 | 0.103 |
| PAF | 1.79 | −1.07 | 0.103 |
| GWY | 1.84 | −1.65 | 0.103 |
| DKH | 1.49 | 6.55 | 0.103 |
| YCT | 1.75 | −0.48 | 0.103 |
| CYT | 1.75 | −0.48 | 0.103 |
| FFS | 2.00 | −2.96 | 0.103 |
| SYF | 1.87 | −1.96 | 0.103 |
| SVF | 1.85 | −1.71 | 0.103 |
| WKI | 1.74 | −0.41 | 0.103 |
| PIF | 1.96 | −2.69 | 0.103 |
| AFC | 1.80 | −1.23 | 0.103 |
| TYS | 1.72 | 0.00 | 0.103 |

TABLE 3-continued

Table S5: peptides from the top 400 $AP_H$

| pep | AP | logP | AP_H |
|---|---|---|---|
| RHS | 1.60 | 2.38 | 0.103 |
| SYW | 1.92 | −2.34 | 0.103 |
| KWH | 1.67 | 0.82 | 0.103 |
| PYM | 1.80 | −1.24 | 0.103 |
| FPG | 1.74 | −0.42 | 0.103 |
| STT | 1.66 | 0.96 | 0.102 |
| TFK | 1.64 | 1.34 | 0.102 |
| VYT | 1.78 | −0.92 | 0.102 |
| FTI | 1.95 | −2.58 | 0.102 |
| NSW | 1.77 | −0.78 | 0.102 |
| TIY | 1.83 | −1.58 | 0.102 |
| SFK | 1.63 | 1.55 | 0.102 |
| MIF | 2.10 | −3.50 | 0.102 |
| CWC | 1.89 | −2.13 | 0.102 |

TABLE 4

Moments of inertia along x, y and z axes, the number of molecules in the largest cluster, the number of clusters, aspect ratio and observed morphology from the final frames of the 1200 ns MD simulations on 1200 peptides in a box.

| Trip | $I_x$ ($10^6$ amu * nm$^2$) | $I_y$ ($10^6$ amu * nm$^2$) | $I_z$ ($10^6$ amu * nm$^2$) | # mol. in largest cluster | number of clusters | Aspect ratio ($I_z/I_x$) | Main morphology |
|---|---|---|---|---|---|---|---|
| CFF | 3.82 | 5.69 | 6.82 | 791 | 6 | 1.79 | Spherical |
| DEN | 0.02 | 0.03 | 0.03 | 31 | 453 | 2.02 | N/A |
| ECG | 0.00 | 0.00 | 0.00 | 4 | 1053 | 2.77 | N/A |
| FFF | 1.70 | 1.80 | 2.40 | 396 | 7 | 1.41 | Sphere/plate |
| FFV | 2.61 | 6.38 | 6.52 | 752 | 2 | 2.49 | Oblong |
| FHF | 5.14 | 13.83 | 14.54 | 802 | 8 | 2.83 | Fibrous$^a$ |
| FYI | 2.68 | 6.07 | 6.30 | 743 | 5 | 2.35 | Oblong |
| FYK | 1.78 | 6.14 | 6.38 | 483 | 6 | 3.59 | Fibrous |
| GGG | 0.00 | 0.00 | 0.00 | 21 | 904 | 3.69 | N/A |
| IYF | 0.91 | 1.09 | 1.19 | 328 | 5 | 1.30 | Spherical |
| KFD | 2.70 | 17.80 | 18.20 | 561 | 5 | 6.75 | Fibrous$^a$ |
| KFF | 0.98 | 5.26 | 5.48 | 406 | 7 | 5.57 | Fibrous |
| KFG | 0.38 | 1.15 | 1.27 | 182 | 44 | 3.37 | Small/fibrous |
| KHD | 14.66 | 60.67 | 69.42 | 1164 | 2 | 4.74 | Fibrous$^a$ |
| KLL | 0.18 | 0.84 | 0.90 | 132 | 221 | 4.93 | N/A |
| KYF | 4.36 | 6.60 | 9.19 | 623 | 5 | 2.11 | Fibrous$^a$ |
| KYW | 3.15 | 8.58 | 10.67 | 491 | 5 | 3.38 | Fibrous$^a$ |
| KYY | 1.25 | 2.19 | 2.58 | 362 | 6 | 2.06 | Spherical |
| LFF | 4.24 | 11.67 | 12.20 | 1002 | 3 | 2.88 | Oblong |
| PFF | 2.66 | 4.64 | 5.17 | 693 | 2 | 1.95 | Spherical/oblong |
| RYF | 1.34 | 6.67 | 6.86 | 406 | 8 | 5.13 | Fibrous |
| VFF | 2.68 | 3.85 | 4.22 | 664 | 4 | 1.57 | Spherical |
| VYV | 0.71 | 0.78 | 0.86 | 311 | 10 | 1.21 | Small/spherical |
| YFI | 1.24 | 2.18 | 2.31 | 433 | 8 | 1.86 | Spherical |

$^a$Due to branching the aspect ratio becomes unrepresentatively low

REFERENCES

1. Zhang, S. G. Fabrication of novel biomaterials through molecular self-assembly. *Nat. Biotechnol.* 21, 1171-1178 (2003).
2. Hartgerink, J. D., Benlash, E. & Stupp, S. L. Self-Assembly and Mineralization of Peptide-Amphiphile Nanofibers. *Science* 294, 1684-1688 (2001).
3. Fletcher, J. M. et al. Self-Assembling Cages from Coiled-Coil Peptide Modules. *Science* 340, 595-599 (2013).
4. O'Leary, L. E. R., Fallas, J. A., Bakota, E. L., Kang, M. K. & Hartgerink, J. D. Multi-hierarchical self-assembly of a collagen mimetic peptide from triple helix to nanofibre and hydrogel. *Nat. Chem.* 3, 821-828 (2011).
5. Reches, M. & Gazit, E. Casting metal nanowires within discrete self-assembled peptide nanotubes. *Science* 300, 625-627 (2003).
6. Ghadiri, M. R., Granja, J. R., Milligan, R. A., McRee, D. E. & Khazanovich, N. Self-assembling organic nanotubes based on a cyclic peptide architecture. *Nature* 366, 324-327 (1993).
7. Zhang, S., Holmes, T., Lockshin, C. & Rich, A. Spontaneous assembly of a self-complementary oligopeptide to form a stable macroscopic membrane. *Proc. Natl. Acad. Sci. U.S.A* 90, 3334-3338 (1993).
8. Reches, M. & Gazit, E. Formation of Closed-Cage Nanostructures by Self-Assembly of Aromatic Dipeptides. *Nano Lett.* 4, 581-585 (2004).
9. Tamamis, P. et al. Self-Assembly of Phenylalanine Oligopeptides: Insights from Experiments and Simulations. *Biophys. J.* 96, 5020-5029 (2009).
10. Marchesan, S., Easton, C. D., Kushkaki, F., Waddington, L. & Hartley, P. G. Tripeptide self-assembled hydrogels: unexpected twists of chirality. *Chem. Commun.* 48, 2195-2197 (2012).
11. Marchesan, S. et al. Unzipping the role of chirality in nanoscale self-assembly of tripeptide hydrogels. *Nanoscale* 4, 6752-6760 (2012).
12. Marchesan, S. et al. Chirality effects at each amino acid position on tripeptide self-assembly into hydrogel biomaterials. *Nanoscale* 6, 5172-5180 (2014).
13. James, J. & Mandal, A. B. The aggregation of Tyr-Phe dipeptide and Val-Tyr-Val tripeptide in aqueous solution and in the presence of SDS and PEO-PPO-PEO tribiock copolymer Fluorescence spectroscopic studies. *J. Colloid Interface Sci.* 360, 600-605 (2011).
14. Moitra, P., Kumar, K., Kondaiah, P. & Bhattacharya, S. Efficacious Anticancer Drug Delivery Mediated by a pH-Sensitive Self-Assembly of a Conserved Tripeptide Derived from Tyrosine Kinase NGF Receptor. *Angew. Chem. Int. Ed.* 53, 1113-1117 (2014).

15. Reches, M., Porat, Y. & Gazit, E. Amyloid Fibril Formation by Pentapeptide and Tetrapeptide Fragments of Human Calcitonin. *J. Biol. Chem.* 277, 35475-35480 (2002).
16. Hauser, C. A. E. et al. Natural tri- to hexapeptides self-assemble in water to amyloid beta-type fiber aggregates by unexpected alpha-helical intermediate structures. *Proc. Natl. Aced. Sci. U.S.A* 108, 1361-1366 (2011).
17. Cao, M., Cao, C., Zhang, L., Xia, D. & Xu, H. Tuning of peptide assembly through force balance adjustment. *J. Colloid Interface Sci.* 407, 287-295 (2013).
18. Zhang, Y., Gu, H., Yang, Z. & Xu, B. Supramolecular Hydrogels Respond to Ligand-Receptor Interaction. *J. Am. Chem. Soc.* 125, 13680-13681 (2003).
19. Smith, A. M. & Ulijn, R. V. Designing peptide based nanomaterials—Chemical Society Reviews (RSC Publishing). *Chem. Soc. Rev.* 37, 664-675 (2008).
20. Das, A. K., Bose, P. P., Drew, M. G. B. & Banerjee, A. The role of protecting groups in the formation of organogels through a nano-fibrillar network formed by self-assembling terminally protected tipeptides. *Tetrahedron* 63, 7432-7442 (2007).
21. Subbalakshmi, C., Manorama, S. V. & Nagaraj, R. Self-assembly of short peptides composed of only aliphatic amino acids and a combination of aromatic and aliphatic amino acids. *J. Pept. Sci.* 18, 283-292 (2012).
22. Yang, Z., Liang, G., Ma, M., Gao, Y. & Xu, B. Conjugates of naphthalene and dipeptides produce molecular hydrogelators with high efficiency of hydrogelation and superhelical nanofibers. *J. Mater. Chem.* 17, 850-854 (2007).
23. Chen, L., Revel, S., Morris, K., C. Serpell, L. & Adams, D. J. Effect of Molecular Structure on the Properties of Naphthalene-Dipeptide Hydrogelators. *Langmuir* 26, 13466-13471 (2010).
24. DeGrado, W. F. & Lear, J. D. Induction of peptide conformation at apolar water interfaces. 1. A study with model peptides of defined hydrophobic periodicity. *J. Am. Chem. Soc.* 107, 7684-7689 (1985).
25. DeGrado, W. F. Design of Peptides and Proteins. *Adv. Protein Chem.* 39, 51-124 (1988).
26. McCullagh, M., Prytkova, T., Tonzani, S., Winter, N. D. & Schatz, G. C. Modeling Self-Assembly Processes Driven by Nonbonded Interactions in Soft Materials†. *J. Phys. Chem. B* 112, 10388-10398 (2008).
27. Lee, O.-S., Cho, V. & Schatz, G. C. Modeling the Self-Assembly of Peptide Amphiphiles into Fibers Using Coarse-Grained Molecular Dynamics. *Nano Lett.* 12, 4907-4913 (2012).
28. Frederix, P. W. J. M., Ulijn, R. V., Hunt, N. T. & Tuttle, T. Virtual Screening for Dipeptide Aggregation: Toward Predictive Tools for Peptide Self-Assembly. *J. Phys. Chem. Lett.* 2, 2380-2384 (2011).
29. Wu, C., Lei, H. & Duan, Y. Formation of Partially Ordered Oligomers of Amyloidogenic Hexapeptide (NF-GAIL) in Aqueous Solution Observed in Molecular Dynamics Simulations. *Biophys. J.* 87, 3000-3009 (2004).
30. Guo, C., Luo, Y., Zhou, R. & Wei, G. Probing the Self-Assembly Mechanism of Diphenylalanine-Based Peptide Nanovesicles and Nanotubes. *ACS Nano* 6, 3907-3918 (2012).
31. Guo, C., Luo, Y., Zhou, R. & Wei, G. Triphenylalanine peptides self-assemble into nanospheres and nanorods that are different from the nanovesicles and nanotubes formed by diphenylalanine peptides. *Nanoscale* (2014). doi: 10.1039/c3nr02505e
32. Thirumalai, D., Klimov, D. & Dima, R. Emerging ideas on the molecular basis of protein and peptide aggregation. *Curr. Opin. Struct. Biol.* 13, 146-159 (2003).
33. Monticelli, L. et al. The MARTINI Coarse-Grained Force Field: Extension to Proteins. *J. Chem. Theory Comput.* 4, 819-834 (2008).
34. Singh, G. & Tieleman, D. P. Using the Wimley-White Hydrophobicity Scale as a Direct Quantitative Test of Force Fields: The MARTINI Coarse-Grained Model. *J. Chem. Theory Comput.* 7, 2316-2324 (2011).
35. De Jong, D. H. et al. Improved Parameters for the Martini Coarse-Grained Protein Force Field. *J. Chem. Theory Comput.* 9, 687-697 (2013).
36. Zaccai, N. R. et al. A de novo peptide hexamer with a mutable channel. *Nat. Chem. Biol.* 7, 935-941 (2011).
37. White, S. H. & Wimley, W. C. Hydrophobic interactions of peptides with membrane interfaces. *Biochim. Biophys. Acta BBA—Rev. Biomembr.* 1376, 339-352 (1998).
38. Wimley, W. C., Creamer, T. P. & White, S. H. Solvation Energies of Amino Acid Side Chains and Backbone in a Family of Host-Guest Pentapeptides†. *Biochemistry (Mosc.)* 35, 5109-5124 (1996).
39. Ash, W. L., Zlomislic, M. R., Oloo, E. O. & Tieleman, D. P. Computer simulations of membrane proteins. *Biochim. Biophys. Acta BBA—Biomembr.* 1666, 158-189 (2004).
40. Yesylevskyy, S. O., Schafer, L. V., Sengupta, D. & Marrink, S. J. Polarizable Water Model for the Coarse-Grained MARTINI Force Field. *PLoS Comput Biol* 6, e1000810 (2010).
41. Lyon, R. P. & Atkins, W. M. Self-Assembly and Gelation of Oxidized Glutathione in Organic Solvents. *J. Am. Chem. Soc.* 123, 4408-4413 (2001).
42. Han, T. H. et al. Bionanosphere Lithography via Hierarchical Peptide Self-Assembly of Aromatic Triphenylalanine. *Small* 6, 945-951 (2010).
43. Cohen, Y., Avram, L. & Frish, L. Diffusion NMR Spectroscopy in Supramolecular and Combinatorial Chemistry: An Old Parameter—New Insights. *Angew. Chem. Int. Ed.* 44, 520-554 (2005).
44. Pouget, E. et al. Elucidation of the Self-Assembly Pathway of Lanreotide Octapeptide into beta-Sheet Nanotubes: Role of Two Stable Intermediates. *J. Am. Chem. Soc.* 132, 4230-4241 (2010).
45. Barth, A. & Zscherp, C. What Vibrations Tell About Proteins. *Q. Rev. Biophys.* 35, 369-430 (2002).
46. Fleming, S. et al. Assessing the Utility of Infrared Spectroscopy as a Structural Diagnostic Tool for β-Sheets in Self-Assembling Aromatic Peptide Amphiphiles. *Langmuir* 29, 9510-9515 (2013).
47. Fuhrmans, M. & Marrink, S.-J. A tool for the morphological analysis of mixtures of lipids and water in computer simulations. *J. Mol. Model.* 17, 1755-1766 (2011).
48. Georgoulia, P. S. & Glykos, N. M. On the Foldability of Tryptophan-Containing Tetra- and Pentapeptides: An Exhaustive Molecular Dynamics Study. *J. Phys. Chem. B* 117, 5522-5532 (2013).
49. Humphrey, W., Dalke, A. & Schulten, K. VMD: Visual molecular dynamics. *J. Mol. Graph.* 14, 33-38 (1996).

FURTHER REFERENCES (1*) Humphrey, W.; Dalke, A.; Schulten, K. *J. Mol. Graph.* 1996, 14, 33.
(2*) marfinize.py. v2.0, accessed 21 Mar. 2013 on www.cgmartini.nl (3*) Hess, B.; Kutzner, C.; van der Spoel, D.; Lindahl, E. *J. Chem. Theory Comput.* 2008, 4, 435.
(4*) Berendsen, H. J. C.; Postma, J. P. M.; van Gunsteren, W. F.; DiNola, A.; Haak, J. R. *J. Chem. Phys.* 1984, 81, 3684.
(5*) Hess, B. *J. Chem. Theory Comput.* 2008, 4, 116.
(6*) Marrink, S. J.; Risselada, H. J.; Yefimov, S.; Tieleman, D. P.; de Vries, A. H. *J. Phys. Chem. B* 2007, 111, 7812.
(7*) Marrink, S. J.; de Vries, A. H.; Mark, A. E. *J. Phys. Chem. B* 2004, 108, 750.
(8*) Yesylevskyy, S. O.; Schafer, L. V.; Sengupta, D.; Marrink, S. *J. PLoS Comput Biol* 2010, 6, e1000810.
(9*) Barth, A.; Zscherp, C. *Q. Rev. Biophys.* 2002, 35, 369.
(10*) Fleming, S.; Frederix, P. W. J. M.; Ramos Sasselli, I.; Hunt, N. T.; Ulijn, R. V.; Tuttle, T. *Langmuir* 2013, 29, 9510.

The invention claimed is:

1. A hydrogel comprising a self-aggregated tripeptide, wherein the self-aggregated tripeptide is selected from the group consisting of KFF, KFY, KFW, FYF, KYY, KYW, KWF, KWY, and KWW.

2. The hydrogel according to claim 1, wherein the hydrogel further comprises an additional self-aggregated tripeptide selected from the group consisting of KFF, KFY, KFW, FYF, KYY, KYW, KWF, KWY, and KWW.

3. The hydrogel according to claim 1, wherein the hydrogel is a self-supporting structure.

4. The hydrogel according to claim 1, further comprising a pharmaceutically active agent.

5. The hydrogel according to claim 1, wherein the self-aggregated tripeptide is present at a concentration of between 1-500 nM.

6. The hydrogel according to claim 1, wherein the self-aggregated tripeptide is KYF.

7. The hydrogel according to claim 1, wherein the self-aggregated tripeptide is KFF.

8. The hydrogel according to claim 1, wherein the self-aggregated tripeptide is KYW.

9. The hydrogel according to claim 1, wherein the self-aggregated tripeptide is KYY.

* * * * *